US006448376B1

(12) United States Patent
La Thangue et al.

(10) Patent No.: US 6,448,376 B1
(45) Date of Patent: ***Sep. 10, 2002

(54) TRANSCRIPTION FACTOR-E2F-5

(75) Inventors: Nicholas B. La Thangue, London (GB); Rene Bernards; Eleonore M. Hijmans, both of Amsterdam (NL)

(73) Assignee: Prolifix Limited, Oxfordshire (GB)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/894,139
(22) PCT Filed: Apr. 18, 1995
(86) PCT No.: PCT/GB95/00869
§ 371 (c)(1),
(2), (4) Date: Aug. 13, 1997
(87) PCT Pub. No.: WO96/25494
PCT Pub. Date: Aug. 22, 1996

(30) Foreign Application Priority Data

Feb. 14, 1995 (GB) ............................................. 9502873

(51) Int. Cl.⁷ ........................... C07K 14/00; C12Q 1/00
(52) U.S. Cl. ........................ 530/350; 530/300; 530/324; 435/4
(58) Field of Search ................................ 530/350, 300, 530/324; 435/4

(56) References Cited

FOREIGN PATENT DOCUMENTS

WO          WO 96/15243          5/1996

OTHER PUBLICATIONS

Ginsberg et al, (Genes Dev., 8:2665–2679), 1994.*
Reiger et al (Glossary of Genetics and Cytogenetics, Classical and Molecular, 4th Ed., Springer–Verlag, Berlin), 1976.*
Buck et al, Oncogene, Jan., 1995, 11:31–38.*
Bernards et al, "Identification and Cloning of Proteins That Associate With P107, a Relative of the Retinoblastoma Protein", EMBL Conference, Oncogenes and Growth Control, Heidelberg, p. 22 (1994).

* cited by examiner

*Primary Examiner*—Susan Ungar
(74) *Attorney, Agent, or Firm*—Nixon & Vanderhye P.C.

(57) ABSTRACT

Two novel transcription factors belonging to the E2F gene family, are disclosed. These are human and murine E2F-5. They can interact with DP-1 and p130.

11 Claims, 15 Drawing Sheets

Fig. 1A.

```
     GGGCCCGACCACCGCGGGGACCGGATGGGGCCGGGGGGCCCCGAGCTCGGGCAGGGCCCCGAGGGCCAGGGCCCCCAGGGCCAGGGCCCAGGGGCCCGGC   100
                                   M  G  P  G  G  P  E  L  G  Q  G  P  R  A  P  G  Q  G  Q  G  Q  R  P  P

101  CGCCCGCAGCCTCCGCAGGCGCAAGCCCCCGCAGCCGCCGCGGGGCCGCAGCCGCCGCAGCCGCCGCAGCCGCCGCAGCCGCCGCAGAGAGCCTGGGCT   200
      P  P  Q  A  Q  A  P  Q  P  P  P  Q  P  P  P  Q  L  G  G  A  G  G  G  S  R  H  E  K  S  L  G  L

201  GCTCACTACCAAGTTCGTGTCGCTGCTGCAGGAGGGCAAGGACGGGTTCTGAAGCGGTTCTGATACTTTGGCTGTGAGGCAAAAAGGAGA   300
      L  T  T  K  F  V  S  L  L  Q  E  A  K  D  G  V  L  D  L  K  A  A  D  T  L  A  V  R  Q  K  R  R

301  ATTTATGATATCACCAATGTCTTAGAGGGAATTGACTTGATTGAAAAAAGTCAAAAAAACAGTATCCAGTGGAAAGGTGTAGGTGCTGGCTGTAATACTA   400
      I  Y  D  I  T  N  V  L  E  G  I  D  L  I  E  K  K  S  K  N  S  I  Q  W  K  G  V  G  A  G  C  N  T  K

401  AAGAGAGTCATAGATAGATTAAGATATCTTAAAGCTGAAATTGAAGATCTAGAAGAAGAGAACTTGATCAGCAGAAGTTGTGGCTACAGCAAAG   500
      E  V  I  D  R  L  R  Y  L  K  A  E  I  E  D  L  E  L  K  E  R  E  L  D  Q  Q  K  L  W  L  Q  Q  S

501  CATCAAAAATGTGATGGACGATTCCATTAATAATAGATTTTCCTATGTAACTCATGAAGACATCTGTAATTGCTTTAATGGTATACACTTTTGGCCATT   600
      I  K  N  V  M  D  D  S  I  N  N  R  F  S  Y  V  T  H  E  D  I  C  N  C  F  N  G  D  T  L  L  A  I

601  CAGGCACCTTCTGGTACACAACTGGAGGTACCATTCCAGAAATGGACAAAAGAATACCAGATCAATCTAAAGAGTCATTCAGGACCTA   700
      Q  A  P  S  G  T  Q  L  E  V  P  I  P  E  M  G  Q  N  G  Q  K  K  Y  Q  I  N  L  K  S  H  S  G  P  I

701  TCCATGTGCTGCTTATAAATAAAGAGTCGAGTTCATCTAAGCCCGTGGTTTTCCCTGTCCCCCACCTGATGACCTCACACAGCCTTCCTCCCAGTCCTT   800
      H  V  L  L  I  N  K  E  S  S  S  K  P  V  V  F  P  V  P  P  P  D  D  L  T  Q  P  S  S  Q  S  L
```

Fig.1A-1

```
801  GACTCCAGTGACTCCACAGAAATCCAGCATGGCAACTCAAATCTGCCTGAGCAACATGTCTGAAAGAAGCCAGGCTCTGCAGCAGACATCAGCTACA
      T  P  V  T  P  Q  K  S  S  M  A  T  Q  N  L  P  E  Q  H  V  S  E  R  S  Q  A  L  Q  Q  T  S  A  T

901  GATATATCTTCAGCAGGATCTATTAGTGGAGATATCATTGATGAGTTAATGTCTTCTGACGTGTTTCCTCTCTTAAGGCTTCTCCTACCCGGCAGATG
      D  I  S  S  A  G  S  I  S  G  D  I  I  D  E  L  M  S  S  D  V  F  P  L  L  R  L  S  P  T  P  A  D  D

1001 ACTACAACTTAATTTAGATGATAACGAAGGAGTTTGTGATGTCCAGATACTAAATTATTAGATTCCAIGGAAACTTGGGACTGTATCTA
      Y  N  F  N  L  D  D  N  E  G  V  C  D  L  F  D  V  Q  I  L  N  Y  *

1101 CCTCTAACTGTGTAACATTTAGACTTCTTAATAACCTAAATATTAAAATAATGAATGTAACACCTTTTTAGTTCACTGATTCTGAAGTGTTCTTCCC

1201 TAATACTTCTTTACTTCACAAACTTCAACCATAAAAACAAAGGGCTCTGATTGCTTAGGGATAAGTGATTAATATTCACAAACGTCCCACTCCC

1301 AAAAGTAACTATATCTGGATTTCAACTTTCTCTAATTGTGAATCCTCCGTTTTTCTTCTTAAGGAGAAGTTAAAGGACTACAGGTCATCAA

1401 AAACAAGTGGCCAAGGACTCATTACTGTCTTATATTTTACTGCCACTAAACTGCCTGTATTTCTGTATGTCCTTCTATCCAAACAGACGTTCACTGC

1501 CACTTGTAAAGTGAAGGATGTAAACGAGGAGATATATAACTGTTCAGTGAACAGATTTTGTGAAGTGCCTTCTGTTTTAGCACTTTAAGTTATCACATTT

1601 TGTTGACTTCTGACATTCCACTTTCCTAGGTTATAGGAAAGATCTGTTTATGTAGTTGTTGTTTTAAAATGTGCCAATGCCTGTACATTAACAAGATTTTT

1701 AAAAATAAAATTGTATAAAACATTAAAAAAAAAAAAAAAAAAAAAAA
                                              1748
```

Fig.9A.

```
AGGGCCCGGCGGGTGATGGCCGCGGAGCCCACGAGCTCTGCTCAGCCACCGCCAGGCTCAGCCGCCCGCCGCCATGGGCG        90
                  M  A  A  E  P  T  S  S  A  Q  P  T  P  Q  A  Q  A  Q  P  P  H  G  A>

CCATCCTCGCAGCCGTCGCGGGGGCCGCTCCGCGGGCAGCCAGCCGGCACGAGAAGAGCCTGGCTTGCTTACCACCAAATTCGTGTCGTTG   180
 P  S  S  Q  P  S  R  R  S  R  G  G  S  S  R  H  E  K  S  L  G  L  L  T  T  K  F  V  S  L>

CTGCAGGAGGCGCAGGACGGGGTGTTCCTGGATCTCAAAGCGGCTGCAGATACCTTGGCTGTGAGGCAAAAGCGAAGAATTTATGATATCACC   270
 L  Q  E  A  Q  D  G  V  L  D  L  K  A  A  A  D  T  L  A  V  R  Q  K  R  R  I  Y  D  I  T>

AATGTCTTAGAGGGAATTGATCTAATTGAAAAAAAATCAAAGAACAGTATCCAGTGGAAGGGTGTAGGTGCTGGCTGTAATACTAAAGAA   360
 N  V  L  E  G  I  D  L  I  E  K  K  S  K  N  S  I  Q  W  K  G  V  G  A  G  C  N  T  K  E>

GTTATCGATAGATTAAGGTGTCTCTTAAAGCTGTGTCTTAAAGCTGAAATTGAAGATCTCGAATTGAAGAAAGAGAACTTGACCAGAAGTTGTGGCTACAG   450
 V  I  D  R  L  R  C  L  K  A  E  I  E  D  L  E  L  K  E  R  E  L  D  Q  Q  K  L  W  L  Q>

CAAAGCATCAAAAATGTGATGGAAGACTCCATTAATAACAGATTTCTTATGTAACTCACGAAGACATCTGCAATTGCTTTCATGGTGAT   540
 Q  S  I  K  N  V  M  E  D  S  I  N  N  R  F  S  Y  V  T  H  E  D  I  C  N  C  F  H  G  D>

ACACTGTTGGCCATTCAGGCACCCTTCTGGTACACAGCTGGAAGTACCTATTCCAGAAATGGGACAGAATGGGACAAAAGAAATACCAGATA   630
 T  L  A  I  Q  A  P  S  G  T  Q  L  E  V  P  I  P  E  M  G  Q  N  G  Q  K  K  Y  Q  I>
```

Fig.9A-1

```
AATCTGAAGAGTCACTCAGGGCCTATCCATGTGCTACTTATAAATAAAGAGTCCAGTTCATCTAAGCCAGTGGTTTTCCTGTTCCCCA    720
 N  L  K  S  H  S  G  P  I  H  V  L  L  I  N  K  E  S  S  S  S  K  P  V  V  F  P  V  P  P'
CCTGATGACCTCACACAGCCTTCCTCCCAGTCCTCAACTTCAGTGACTCCACAGAAATCCACCATGGCTGCTCAAAACCTGCTGAGCAG    810
 P  D  D  L  T  Q  P  S  S  Q  S  S  T  S  V  T  P  Q  K  S  T  M  A  A  Q  N  L  P  E  Q'
CATGTTTCCGAAAGAAGCCAGACTTTCCAGCAGAGACACCAGCTGCAGAAGTATCTTCAGGATCTATTAGTGGAGACATCATTGATGAACTG    900
 H  V  S  E  R  S  Q  T  F  Q  Q  T  P  A  A  E  V  S  S  G  S  I  S  G  D  I  I  D  E  L'
ATGTCTTCTGATGTGTTCCCTCTTTTACGGCTTTCCCCTACCCCAGCAGATGACTACAACTTTAATTTAGATGATAATGAAGGAGTTTGT    990
 M  S  S  D  V  F  P  L  L  R  L  S  P  T  P  A  D  D  Y  N  F  N  L  D  D  N  E  G  V  C'
GATCTGTTTGATGTTCAGATACTAAATTATTAGATTCCATGGAAACTTGGGACTATTATTCTACCTCTATAACATTTAGAATTCTTTAAT   1080
 D  L  F  D  V  Q  I  L  N  Y  •
AACCTAAGTATTTAAAATTATGAATGTAACACCTTTTTAGTTCACTGATTCTGAAGTGTTCTTCCCTAACATTTTATTTTTACTTCACA   1170
AAACTTGAAAGGGATATGCTGCTTCTGGGGGTAGAGGTAAGATTACCTGTCCAGCAGCTGCCCCTCCAGTGACCACATTCAGTTTCTTT   1260
CAGTAGCTTCCTCTCCTGAGAGGCAGTTACAGCAGGCTCAGTTCATCCAAACAAAACATTGTCAGAAGTACACTTATTG   1325
```

Fig. 9C.

DNA Binding / Dimerization

```
E2F-1      KSPGEKSRYETSLNLTTKRFLELLSHSADGVVDLNWAAEVLKV.QKRRIYDITNVLEGIQLIAKKSKNHIQWLGS
E2F-2      KSPGEKTRYDTSLGLLTKKPIYLLSESEDGVLDLNWAAEVLDV.QKRRIYDITNVLEGIQLIRKKAKNNIQWVGR
E2F-3      KSPSEKTRYDTSLGLLTKKFIQLLSQSPDGVLDLNKAAEVLKV.QKRRIYDITNVLEGIHLIKKKSKNNVQWMGC
E2F-4      ......SRHEKSLGLITTKFVSLLQEAKDGVLDLRLAADTLAVRQKRRIYDITNVLEGIGLLEKQSKNSIQWRGV
E2F-5   33 RSRGGSSRHEKSLGLITTKFVSLLQEAQDGVLDLKAAADTLAVEQKRRIYDITNVLEGIDLIEKKSKNSIQWKGV 107
DP-1       SMKVCEKQRKGTTSYNEVADELVAEFSAADNHILPNESAYDQKNIRRVYDALNVLMAMNIISK.EKKEIKWIGL
```

Leucine Zip

```
E2F-1      LTQDLRQLQESEQQLDHLMNICTTQLRLL
E2F-2      LGQELKELMNTEQALDQLIQSCSLSFKHL
E2F-3      LSKEVTELSQEEKKLDELIQSCTLDLKLL
E2F-4      LKAEIEELQQREQELDQHKMWMQQSIRNV
E2F-5  123 LKAEIEDLELKERELDQQLMLQQSIRNV 151
```

Marked Box

```
E2F-1      NFQISLKSKQGPIDVFLCPEE
E2F-2      NLQIYLKSTQGPIEVYLCPEE
E2F-3      SLQIHLASIQGPIEVYLCPEE
E2F-4      KYQIHLRSVSGPIEVLLVNKE
E2F-5  202 KYQINLKSHSGPIHVLLINKE 222
```

Pocket Protein Binding

```
E2F-1      ALDYHFGLEEGEGIRDLFD
E2F-2      QDDYLWGLEAGEGISDLFD
E2F-3      QEDYLLSLGEEBGISDLFD
E2F-4  312 DHDYIYNLDESEGVQDLFD
E2F-5      D.DYNFNLDNEGVQDLFD 329
```

Fig. 10.
A  Reporters
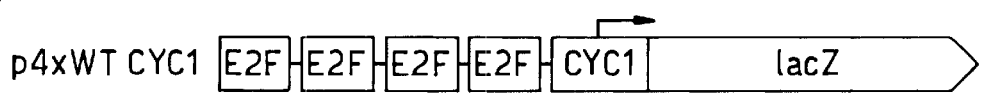
Effectors
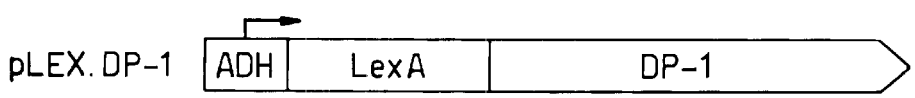
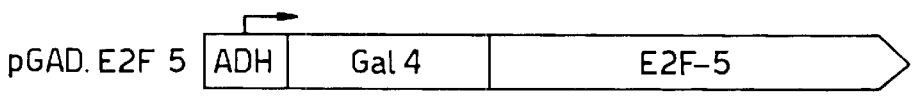
B
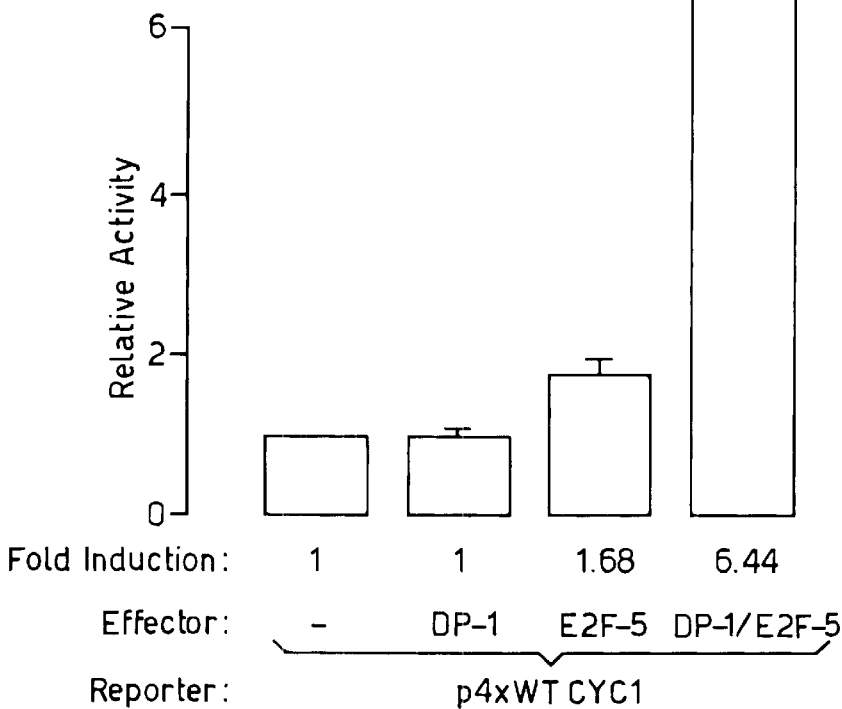

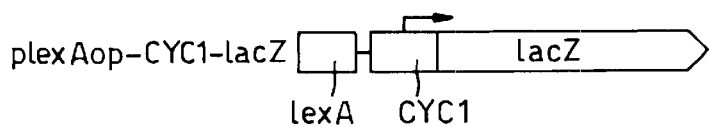
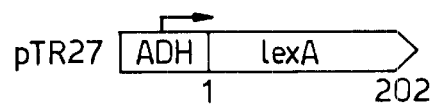
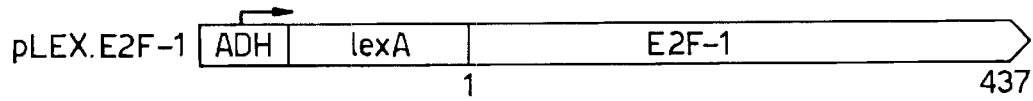
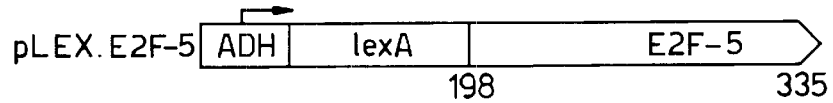
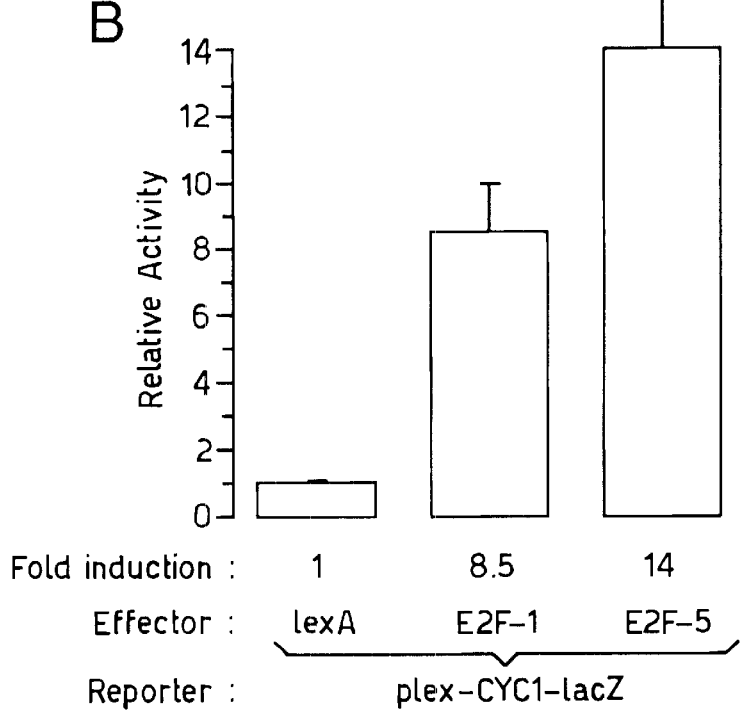
Fig. 11.

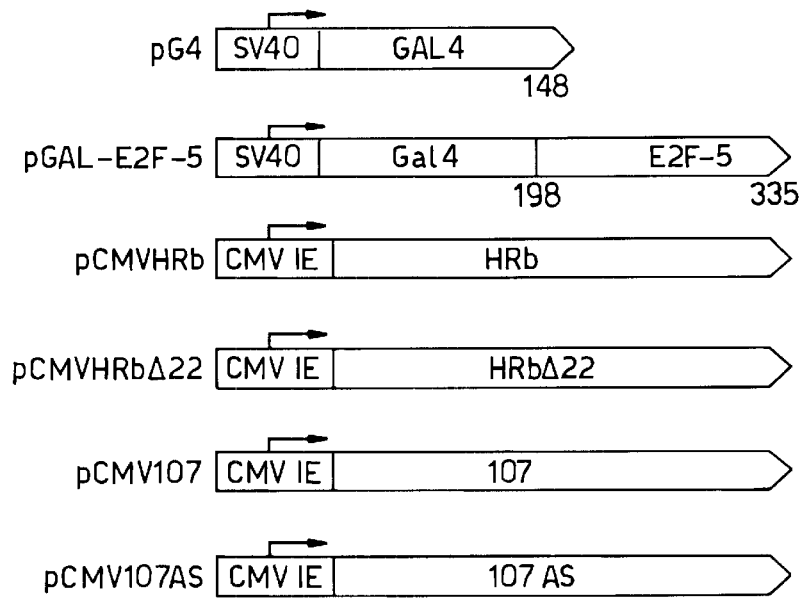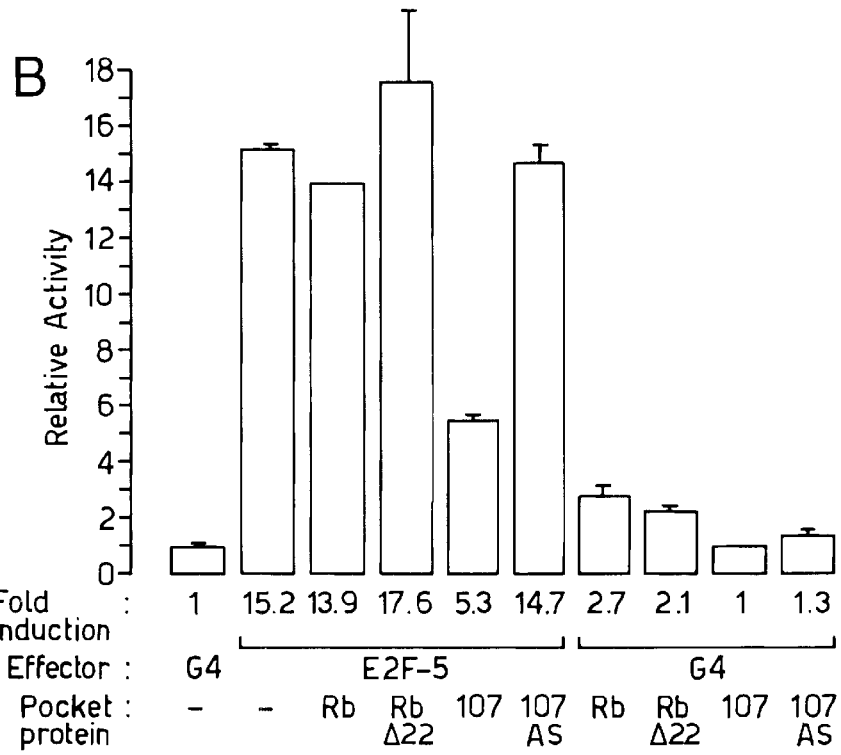
Fig. 12.

SEQUENCE LISTING (1) GENERAL INFORMATION:

(iii) NUMBER OF SEQUENCES: 25

(2) INFORMATION FOR SEQ ID NO: 1:

(i) SEQUENCE CHARACTERISTICS:
      (A) LENGTH: 1748 base pairs
      (B) TYPE: nucleic acid
      (C) STRANDEDNESS: double
      (D) TOPOLOGY: linear (ii) MOLECULE TYPE: DNA (genomic)

(ix) FEATURE:
      (A) NAME/KEY: CDS
      (B) LOCATION:31..1068

(xi) SEQUENCE DESCRIPTION: SEQ ID NO: 1:

```
GGGGCCCGAC CACCGCGGGG CCGGGACGCG ATG GCG GCG GCA GAG CCC GCG AGC        54
                                Met Ala Ala Ala Glu Pro Ala Ser
                                 1               5

TCG GGC CAG CAG GCG CCG GCA GGG CAG GGG CAG GGC CAG CGG CCG CCG       102
Ser Gly Gln Gln Ala Pro Ala Gly Gln Gly Gln Gly Gln Arg Pro Pro
    10                  15                  20

CCG CAG CCT CCG CAG GCG CAA GCC CCG CAG CCG CCC CCG CCG CCG CAG       150
Pro Gln Pro Pro Gln Ala Gln Ala Pro Gln Pro Pro Pro Pro Pro Gln
 25                  30                  35                  40

CTC GGG GGC GCG GGG GGC GGC AGC AGC AGG CAC GAG AAG AGC CTG GGG       198
Leu Gly Gly Ala Gly Gly Gly Ser Ser Arg His Glu Lys Ser Leu Gly
                 45                  50                  55

CTG CTC ACT ACC AAG TTC GTG TCG CTG CTG CAG GAG GCC AAG GAC GGC       246
Leu Leu Thr Thr Lys Phe Val Ser Leu Leu Gln Glu Ala Lys Asp Gly
             60                  65                  70

GTT CTG GAT CTC AAA GCG GCT GCT GAT ACT TTG GCT GTG AGG CAA AAA       294
```

-continued

```
Val Leu Asp Leu Lys Ala Ala Asp Thr Leu Ala Val Arg Gln Lys
         75                  80                  85

AGG AGA ATT TAT GAT ATC ACC AAT GTC TTA GAG GGA ATT GAC TTG ATT       342
Arg Arg Ile Tyr Asp Ile Thr Asn Val Leu Glu Gly Ile Asp Leu Ile
         90                  95                 100

GAA AAA AAG TCA AAA AAC AGT ATC CAG TGG AAA GGT GTA GGT GCT GGC       390
Glu Lys Lys Ser Lys Asn Ser Ile Gln Trp Lys Gly Val Gly Ala Gly
105                 110                 115                 120

TGT AAT ACT AAA GAA GTC ATA GAT AGA TTA AGA TAT CTT AAA GCT GAA       438
Cys Asn Thr Lys Glu Val Ile Asp Arg Leu Arg Tyr Leu Lys Ala Glu
                125                 130                 135

ATT GAA GAT CTA GAA CTG AAG GAA AGA GAA CTT GAT CAG CAG AAG TTG       486
Ile Glu Asp Leu Glu Leu Lys Glu Arg Glu Leu Asp Gln Gln Lys Leu
            140                 145                 150

TGG CTA CAG CAA AGC ATC AAA AAT GTG ATG GAC GAT TCC ATT AAT AAT       534
Trp Leu Gln Gln Ser Ile Lys Asn Val Met Asp Asp Ser Ile Asn Asn
            155                 160                 165

AGA TTT TCC TAT GTA ACT CAT GAA GAC ATC TGT AAT TGC TTT AAT GGT       582
Arg Phe Ser Tyr Val Thr His Glu Asp Ile Cys Asn Cys Phe Asn Gly
        170                 175                 180

GAT ACA CTT TTG GCC ATT CAG GCA CCT TCT GGT ACA CAA CTG GAG GTA       630
Asp Thr Leu Leu Ala Ile Gln Ala Pro Ser Gly Thr Gln Leu Glu Val
185                 190                 195                 200

CCC ATT CCA GAA ATG GGT CAG AAT GGA CAA AAG AAA TAC CAG ATC AAT       678
Pro Ile Pro Glu Met Gly Gln Asn Gly Gln Lys Lys Tyr Gln Ile Asn
                205                 210                 215

CTA AAG AGT CAT TCA GGA CCT ATC CAT GTG CTG CTT ATA AAT AAA GAG       726
Leu Lys Ser His Ser Gly Pro Ile His Val Leu Leu Ile Asn Lys Glu
            220                 225                 230

TCG AGT TCA TCT AAG CCC GTG GTT TTT CCT GTT CCC CCA CCT GAT GAC       774
Ser Ser Ser Ser Lys Pro Val Val Phe Pro Val Pro Pro Pro Asp Asp
            235                 240                 245

CTC ACA CAG CCT TCC TCC CAG TCC TTG ACT CCA GTG ACT CCA CAG AAA       822
Leu Thr Gln Pro Ser Ser Gln Ser Leu Thr Pro Val Thr Pro Gln Lys
        250                 255                 260

TCC AGC ATG GCA ACT CAA AAT CTG CCT GAG CAA CAT GTC TCT GAA AGA       870
Ser Ser Met Ala Thr Gln Asn Leu Pro Glu Gln His Val Ser Glu Arg
265                 270                 275                 280

AGC CAG GCT CTG CAG CAG ACA TCA GCT ACA GAT ATA TCT TCA GCA GGA       918
Ser Gln Ala Leu Gln Gln Thr Ser Ala Thr Asp Ile Ser Ser Ala Gly
                285                 290                 295

TCT ATT AGT GGA GAT ATC ATT GAT GAG TTA ATG TCT TCT GAC GTG TTT       966
Ser Ile Ser Gly Asp Ile Ile Asp Glu Leu Met Ser Ser Asp Val Phe
            300                 305                 310

CCT CTC TTA AGG CTT TCT CCT ACC CCG GCA GAT GAC TAC AAC TTT AAT      1014
Pro Leu Leu Arg Leu Ser Pro Thr Pro Ala Asp Asp Tyr Asn Phe Asn
            315                 320                 325

TTA GAT GAT AAC GAA GGA GTT TGT GAT CTG TTT GAT GTC CAG ATA CTA      1062
Leu Asp Asp Asn Glu Gly Val Cys Asp Leu Phe Asp Val Gln Ile Leu
        330                 335                 340

AAT TAT TAGATTCCAT GGAAACTTGG GACTGTTATC TACCTCTAAC TGTGTAACAT       1118
Asn Tyr
345

TTTAGACTTC TTAATAACCT AAATATTTAA AATAATGAAT GTAACACCTT TTTTAGTTCA    1178

CTGATTCTGA AGTGTTCTTC CCTAATACTT TCTTTACTTC ACAAAACTTC AACCATAAAA    1238

ACAAAGGGCT CTGATTGCTT TAGGGGATAA GTGATTTAAT ATTCACAAAC GTCCCCACTC    1298

CCAAAAGTAA CTATATTCTG GATTTCAACT TTTCTTCTAA TTGTGAATCC TTCCGTTTTT    1358
```

```
TCTTCTTAAG GAGGAAAGTT AAAGGACACT ACAGGTCATC AAAAACAAGT TGGCCAAGGA    1418

CTCATTACTT GTCTTATATT TTTACTGCCA CTAAACTGCC TGTATTTCTG TATGTCCTTC    1478

TATCCAAACA GACGTTCACT GCCACTTGTA AAGTGAAGGA TGTAAACGAG GATATATAAC    1538

TGTTTCAGTG AACAGATTTT GTGAAGTGCC TTCTGTTTTA GCACTTTAAG TTTATCACAT    1598

TTTGTTGACT TCTGACATTC CACTTTCCTA GGTTATAGGA AGATCTGTT TATGTAGTTT     1658

GTTTTTAAAA TGTGCCAATG CCTGTACATT AACAAGATTT TTAAAAATAA AATTGTATAA    1718

AACATTAAAA AAAAAAAAAA AAAAAAAAA                                      1748
```

(2) INFORMATION FOR SEQ ID NO: 2:

(i) SEQUENCE CHARACTERISTICS:
        (A) LENGTH: 346 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Ala Ala Ala Glu Pro Ala Ser Ser Gly Gln Gln Ala Pro Ala Gly
  1               5                  10                  15

Gln Gly Gln Gly Gln Arg Pro Pro Gln Pro Pro Gln Ala Gln Ala
             20                  25                  30

Pro Gln Pro Pro Pro Pro Gln Leu Gly Gly Ala Gly Gly Gly Ser
         35                  40                  45

Ser Arg His Glu Lys Ser Leu Gly Leu Leu Thr Thr Lys Phe Val Ser
     50                  55                  60

Leu Leu Gln Glu Ala Lys Asp Gly Val Leu Asp Leu Lys Ala Ala Ala
 65                  70                  75                  80

Asp Thr Leu Ala Val Arg Gln Lys Arg Arg Ile Tyr Asp Ile Thr Asn
                 85                  90                  95

Val Leu Glu Gly Ile Asp Leu Ile Glu Lys Ser Lys Asn Ser Ile
            100                 105                 110

Gln Trp Lys Gly Val Gly Ala Gly Cys Asn Thr Lys Glu Val Ile Asp
            115                 120                 125

Arg Leu Arg Tyr Leu Lys Ala Glu Ile Glu Asp Leu Glu Leu Lys Glu
130                 135                 140

Arg Glu Leu Asp Gln Gln Lys Leu Trp Leu Gln Gln Ser Ile Lys Asn
145                 150                 155                 160

Val Met Asp Asp Ser Ile Asn Asn Arg Phe Ser Tyr Val Thr His Glu
                165                 170                 175

Asp Ile Cys Asn Cys Phe Asn Gly Asp Thr Leu Leu Ala Ile Gln Ala
            180                 185                 190

Pro Ser Gly Thr Gln Leu Glu Val Pro Ile Pro Glu Met Gly Gln Asn
            195                 200                 205

Gly Gln Lys Lys Tyr Gln Ile Asn Leu Lys Ser His Ser Gly Pro Ile
210                 215                 220

His Val Leu Leu Ile Asn Lys Glu Ser Ser Ser Lys Pro Val Val
225                 230                 235                 240

Phe Pro Val Pro Pro Asp Asp Leu Thr Gln Pro Ser Ser Gln Ser
                245                 250                 255

Leu Thr Pro Val Thr Pro Gln Lys Ser Ser Met Ala Thr Gln Asn Leu
            260                 265                 270

Pro Glu Gln His Val Ser Glu Arg Ser Gln Ala Leu Gln Gln Thr Ser
            275                 280                 285
```

```
Ala Thr Asp Ile Ser Ser Ala Gly Ser Ile Ser Gly Asp Ile Ile Asp
    290                 295                 300

Glu Leu Met Ser Ser Asp Val Phe Pro Leu Leu Arg Leu Ser Pro Thr
305                 310                 315                 320

Pro Ala Asp Asp Tyr Asn Phe Asn Leu Asp Asp Asn Glu Gly Val Cys
                325                 330                 335

Asp Leu Phe Asp Val Gln Ile Leu Asn Tyr
            340                 345
```

(2) INFORMATION FOR SEQ ID NO: 3:

(i) SEQUENCE CHARACTERISTICS:
        (A) LENGTH: 1340 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION:16..1020

(xi) SEQUENCE DESCRIPTION: SEQ ID NO: 3:

```
AGGGCCGCGG CGGTG ATG GCG GCG GCG GAG CCC ACG AGC TCT GCT CAG CCC        51
              Met Ala Ala Ala Glu Pro Thr Ser Ser Ala Gln Pro
                       350                 355

ACG CCG CAG GCC CAG GCT CAG CCG CCG CCG CAT GGG GCG CCA TCC TCG         99
Thr Pro Gln Ala Gln Ala Gln Pro Pro Pro His Gly Ala Pro Ser Ser
        360                 365                 370

CAG CCG TCG CGG CGC TCG CGG GGG GGC AGC AGC CGG CAC GAG AAG AGC        147
Gln Pro Ser Arg Arg Ser Arg Gly Gly Ser Ser Arg His Glu Lys Ser
375                 380                 385                 390

CTG GGC TTG CTT ACC ACC AAA TTC GTG TCG TTG CTG CAG GAG GCG CAG        195
Leu Gly Leu Leu Thr Thr Lys Phe Val Ser Leu Leu Gln Glu Ala Gln
                395                 400                 405

GAC GGC GTC CTG GAT CTC AAA GCG GCT GCA GAT ACC TTG GCT GTG AGG        243
Asp Gly Val Leu Asp Leu Lys Ala Ala Ala Asp Thr Leu Ala Val Arg
        410                 415                 420

CAA AAG CGA AGA ATT TAT GAT ATC ACC AAT GTC TTA GAG GGA ATT GAT        291
Gln Lys Arg Arg Ile Tyr Asp Ile Thr Asn Val Leu Glu Gly Ile Asp
425                 430                 435

CTA ATT GAA AAA AAA TCA AAG AAC AGT ATC CAG TGG AAG GGT GTA GGT        339
Leu Ile Glu Lys Lys Ser Lys Asn Ser Ile Gln Trp Lys Gly Val Gly
        440                 445                 450

GCT GGC TGT AAT ACT AAA GAA GTT ATC GAT AGA TTA AGG TGT CTT AAA        387
Ala Gly Cys Asn Thr Lys Glu Val Ile Asp Arg Leu Arg Cys Leu Lys
455                 460                 465                 470

GCT GAA ATT GAA GAT CTC GAA TTG AAG GAA AGA GAA CTT GAC CAG CAG        435
Ala Glu Ile Glu Asp Leu Glu Leu Lys Glu Arg Glu Leu Asp Gln Gln
                475                 480                 485

AAG TTG TGG CTA CAG CAA AGC ATC AAA AAT GTG ATG GAA GAC TCC ATT        483
Lys Leu Trp Leu Gln Gln Ser Ile Lys Asn Val Met Glu Asp Ser Ile
        490                 495                 500

AAT AAC AGA TTT TCT TAT GTA ACT CAC GAA GAC ATC TGC AAT TGC TTT        531
Asn Asn Arg Phe Ser Tyr Val Thr His Glu Asp Ile Cys Asn Cys Phe
            505                 510                 515

CAT GGT GAT ACA CTG TTG GCC ATT CAG GCA CCT TCT GGT ACA CAG CTG        579
His Gly Asp Thr Leu Leu Ala Ile Gln Ala Pro Ser Gly Thr Gln Leu
        520                 525                 530

GAA GTA CCT ATT CCA GAA ATG GGA CAG AAT GGA CAA AAG AAA TAC CAG        627
```

```
Glu Val Pro Ile Pro Glu Met Gly Gln Asn Gly Gln Lys Lys Tyr Gln
535                 540                 545                 550

ATA AAT CTG AAG AGT CAC TCA GGG CCT ATC CAT GTG CTA CTT ATA AAT      675
Ile Asn Leu Lys Ser His Ser Gly Pro Ile His Val Leu Leu Ile Asn
                555                 560                 565

AAA GAG TCC AGT TCA TCT AAG CCA GTG GTT TTT CCT GTT CCC CCA CCT      723
Lys Glu Ser Ser Ser Ser Lys Pro Val Val Phe Pro Val Pro Pro Pro
                570                 575                 580

GAT GAC CTC ACA CAG CCT TCC TCC CAG TCC TCA ACT TCA GTG ACT CCA      771
Asp Asp Leu Thr Gln Pro Ser Ser Gln Ser Ser Thr Ser Val Thr Pro
                585                 590                 595

CAG AAA TCC ACC ATG GCT GCT CAA AAC CTG CCT GAG CAG CAT GTT TCC      819
Gln Lys Ser Thr Met Ala Ala Gln Asn Leu Pro Glu Gln His Val Ser
                600                 605                 610

GAA AGA AGC CAG ACT TTC CAG CAG ACA CCA GCT GCA GAA GTA TCT TCA      867
Glu Arg Ser Gln Thr Phe Gln Gln Thr Pro Ala Ala Glu Val Ser Ser
615                 620                 625                 630

GGA TCT ATT AGT GGA GAC ATC ATT GAT GAA CTG ATG TCT TCT GAT GTG      915
Gly Ser Ile Ser Gly Asp Ile Ile Asp Glu Leu Met Ser Ser Asp Val
                635                 640                 645

TTT CCT CTT TTA CGG CTT TCT CCT ACC CCA GCA GAT GAC TAC AAC TTT      963
Phe Pro Leu Leu Arg Leu Ser Pro Thr Pro Ala Asp Asp Tyr Asn Phe
                650                 655                 660

AAT TTA GAT GAT AAT GAA GGA GTT TGT GAT CTG TTT GAT GTT CAG ATA     1011
Asn Leu Asp Asp Asn Glu Gly Val Cys Asp Leu Phe Asp Val Gln Ile
                665                 670                 675

CTA AAT TAT TAGATTCCAT GGAAACTTGG GACTATTATC TACCTCTATA             1060
Leu Asn Tyr
    680

ACATTTTAGA ATTCTTTAAT AACCTAAGTA TTTAAAATTA TGAATGTAAC ACCTTTTTAG   1120

TTCACTGATT CTGAAGTGTT CTTCCCTAAC ATTTTATTTT TTACTTCACA AAACTTGAAA   1180

GGGATATGCT GCTTCTGGGG GGTAGAGGTA AGATTACCTG TCCAGCAGCT GCCCCTCCAG   1240

TGACCACATT CAGTTTCTTT CAGTAGCTTC CTCTCCTGAG AGGCAGTTAC AGCAGGCTCA   1300

GTTCATCCAA ACAAAACATT GTCAGAAGTA CACTTATTTG                        1340

(2) INFORMATION FOR SEQ ID NO: 4:

(i) SEQUENCE CHARACTERISTICS:
        (A) LENGTH: 335 amino acids
        (B) TYPE: amino acid
        (D) TOPOLOGY: linear (ii) MOLECULE TYPE: protein (xi) SEQUENCE DESCRIPTION: SEQ ID NO: 4:

Met Ala Ala Ala Glu Pro Thr Ser Ser Ala Gln Pro Thr Pro Gln Ala
1               5                   10                  15

Gln Ala Gln Pro Pro His Gly Ala Pro Ser Ser Gln Pro Ser Arg
            20                  25                  30

Arg Ser Arg Gly Gly Ser Ser Arg His Glu Lys Ser Leu Gly Leu Leu
        35                  40                  45

Thr Thr Lys Phe Val Ser Leu Leu Gln Glu Ala Gln Asp Gly Val Leu
    50                  55                  60

Asp Leu Lys Ala Ala Ala Asp Thr Leu Ala Val Arg Gln Lys Arg Arg
65                  70                  75                  80

Ile Tyr Asp Ile Thr Asn Val Leu Glu Gly Ile Asp Leu Ile Glu Lys
                85                  90                  95
```

-continued

```
Lys Ser Lys Asn Ser Ile Gln Trp Lys Gly Val Gly Ala Gly Cys Asn
        100                 105                 110

Thr Lys Glu Val Ile Asp Arg Leu Arg Cys Leu Lys Ala Glu Ile Glu
        115                 120                 125

Asp Leu Glu Leu Lys Glu Arg Glu Leu Asp Gln Gln Lys Leu Trp Leu
        130                 135                 140

Gln Gln Ser Ile Lys Asn Val Met Glu Asp Ser Ile Asn Asn Arg Phe
145                 150                 155                 160

Ser Tyr Val Thr His Glu Asp Ile Cys Asn Cys Phe His Gly Asp Thr
                165                 170                 175

Leu Leu Ala Ile Gln Ala Pro Ser Gly Thr Gln Leu Glu Val Pro Ile
                180                 185                 190

Pro Glu Met Gly Gln Asn Gly Gln Lys Lys Tyr Gln Ile Asn Leu Lys
        195                 200                 205

Ser His Ser Gly Pro Ile His Val Leu Leu Ile Asn Lys Glu Ser Ser
        210                 215                 220

Ser Ser Lys Pro Val Val Phe Pro Val Pro Pro Asp Asp Leu Thr
225                 230                 235                 240

Gln Pro Ser Ser Gln Ser Ser Thr Ser Val Thr Pro Gln Lys Ser Thr
                245                 250                 255

Met Ala Ala Gln Asn Leu Pro Glu Gln His Val Ser Glu Arg Ser Gln
                260                 265                 270

Thr Phe Gln Gln Thr Pro Ala Ala Glu Val Ser Ser Gly Ser Ile Ser
        275                 280                 285

Gly Asp Ile Ile Asp Glu Leu Met Ser Ser Asp Val Phe Pro Leu Leu
        290                 295                 300

Arg Leu Ser Pro Thr Pro Ala Asp Asp Tyr Asn Phe Asn Leu Asp Asp
305                 310                 315                 320

Asn Glu Gly Val Cys Asp Leu Phe Asp Val Gln Ile Leu Asn Tyr
                325                 330                 335
```

(2) INFORMATION FOR SEQ ID NO: 5:

(i) SEQUENCE CHARACTERISTICS:
        (A) LENGTH: 74 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO: 5:

```
Lys Ser Pro Gly Glu Lys Ser Arg Tyr Glu Thr Ser Leu Asn Leu Thr
1               5                   10                  15

Thr Lys Arg Phe Leu Glu Leu Leu Ser His Ser Ala Asp Gly Val Val
                20                  25                  30

Asp Leu Asn Trp Ala Ala Glu Val Leu Lys Val Gln Lys Arg Arg Ile
                35                  40                  45

Tyr Asp Ile Thr Asn Val Leu Glu Gly Ile Gln Leu Ile Ala Lys Lys
            50                  55                  60

Ser Lys Asn His Ile Gln Trp Leu Gly Ser
65                  70
```

(2) INFORMATION FOR SEQ ID NO: 6:

(i) SEQUENCE CHARACTERISTICS:
        (A) LENGTH: 74 amino acids
        (B) TYPE: amino acid (C) STRANDEDNESS:
          (D) TOPOLOGY: linear (ii) MOLECULE TYPE: peptide (xi) SEQUENCE DESCRIPTION: SEQ ID NO: 6:

Lys Ser Pro Gly Glu Lys Thr Arg Tyr Asp Thr Ser Leu Asn Leu Leu
1               5                   10                  15

Pro Lys Lys Phe Ile Tyr Leu Leu Ser Glu Ser Glu Asp Gly Val Leu
                20                  25                  30

Asp Leu Asn Trp Ala Ala Glu Val Leu Lys Val Gln Lys Arg Arg Ile
            35                  40                  45

Tyr Asp Ile Thr Asn Val Leu Glu Gly Ile Gln Leu Ile Arg Lys Lys
    50                  55                  60

Arg Lys Asn His Ile Gln Trp Val Gly Arg
65                  70

(2) INFORMATION FOR SEQ ID NO: 7:

(i) SEQUENCE CHARACTERISTICS:
          (A) LENGTH: 74 amino acids
          (B) TYPE: amino acid
          (C) STRANDEDNESS:
          (D) TOPOLOGY: linear (ii) MOLECULE TYPE: peptide (xi) SEQUENCE DESCRIPTION: SEQ ID NO: 7:

Lys Ser Pro Gly Glu Lys Thr Arg Tyr Asp Thr Ser Leu Asn Leu Leu
1               5                   10                  15

Thr Lys Lys Phe Ile Gln Leu Leu Ser Gln Ser Pro Asp Gly Val Leu
                20                  25                  30

Asp Leu Asn Lys Ala Ala Glu Val Leu Lys Val Gln Lys Arg Arg Ile
            35                  40                  45

Tyr Asp Ile Thr Asn Val Leu Glu Gly Ile His Leu Ile Lys Lys Lys
    50                  55                  60

Ser Lys Asn His Val Gln Trp Met Gly Cys
65                  70

(2) INFORMATION FOR SEQ ID NO: 8:

(i) SEQUENCE CHARACTERISTICS:
          (A) LENGTH: 69 amino acids
          (B) TYPE: amino acid
          (C) STRANDEDNESS:
          (D) TOPOLOGY: linear (ii) MOLECULE TYPE: peptide (xi) SEQUENCE DESCRIPTION: SEQ ID NO: 8:

Ser Arg His Glu Lys Ser Leu Asn Leu Leu Thr Thr Lys Phe Val Gln
1               5                   10                  15

Leu Leu Gln Glu Ala Lys Asp Gly Val Leu Asp Leu Lys Leu Ala Ala
                20                  25                  30

Asp Thr Leu Ala Val Arg Gln Lys Arg Arg Ile Tyr Asp Ile Thr Asn
            35                  40                  45

Val Leu Glu Gly Ile Gly Leu Ile Glu Lys Lys Ser Lys Asn Ser Thr
    50                  55                  60

Gln Trp Arg Gly Val
65

(2) INFORMATION FOR SEQ ID NO: 9:

(i) SEQUENCE CHARACTERISTICS:
        (A) LENGTH: 75 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO: 9:

```
Arg Ser Arg Gly Gly Ser Ser Arg His Glu Lys Ser Leu Gly Leu Leu
 1               5                  10                  15

Thr Thr Lys Phe Val Ser Leu Leu Gln Glu Ala Gln Asp Gly Val Leu
            20                  25                  30

Asp Leu Lys Ala Ala Ala Asp Thr Leu Ala Val Arg Gln Lys Arg Arg
         35                  40                  45

Ile Tyr Asp Ile Thr Asn Val Leu Glu Gly Ile Asp Leu Ile Glu Lys
     50                  55                  60

Lys Ser Lys Asn Ser Ile Gln Trp Lys Gly Val
 65                  70                  75
```

(2) INFORMATION FOR SEQ ID NO: 10:

(i) SEQUENCE CHARACTERISTICS:
        (A) LENGTH: 74 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO: 10:

```
Ser Met Lys Val Cys Glu Lys Gln Arg Lys Gly Thr Thr Ser Tyr Asn
 1               5                  10                  15

Glu Val Ala Asp Glu Leu Val Ala Glu Phe Ser Ala Ala Asp Asn His
            20                  25                  30

Ile Leu Pro Asn Glu Ser Ala Tyr Asp Gln Lys Asn Ile Arg Arg Arg
         35                  40                  45

Val Tyr Asp Ala Leu Asn Val Leu Met Ala Met Asn Ile Ile Ser Lys
     50                  55                  60

Glu Lys Lys Glu Ile Lys Trp Ile Gly Leu
 65                  70
```

(2) INFORMATION FOR SEQ ID NO: 11:

(i) SEQUENCE CHARACTERISTICS:
        (A) LENGTH: 29 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO: 11:

```
Leu Thr Gln Asp Leu Arg Gln Leu Gln Glu Ser Glu Gln Gln Leu Asp
 1               5                  10                  15

His Leu Met Asn Ile Cys Thr Thr Gln Leu Arg Leu Leu
            20                  25
```

(2) INFORMATION FOR SEQ ID NO: 12:

(i) SEQUENCE CHARACTERISTICS:
        (A) LENGTH: 29 amino acids (B) TYPE: amino acid
            (C) STRANDEDNESS:
            (D) TOPOLOGY: linear (ii) MOLECULE TYPE: peptide (xi) SEQUENCE DESCRIPTION: SEQ ID NO: 12:

Leu Gly Gln Glu Leu Lys Glu Leu Met Asn Thr Glu Gln Ala Leu Asp
1               5                   10                  15

Gln Leu Ile Gln Ser Cys Ser Leu Ser Phe Lys His Leu
            20                  25

(2) INFORMATION FOR SEQ ID NO: 13:

(i) SEQUENCE CHARACTERISTICS:
        (A) LENGTH: 29 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO: 13:

Leu Ser Lys Glu Val Thr Glu Leu Ser Gln Glu Lys Lys Leu Asp
1               5                   10                  15

Glu Leu Ile Gln Ser Cys Thr Leu Asp Leu Lys Leu Leu
            20                  25

(2) INFORMATION FOR SEQ ID NO: 14:

(i) SEQUENCE CHARACTERISTICS:
        (A) LENGTH: 29 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO: 14:

Leu Lys Ala Glu Ile Glu Glu Leu Gln Gln Arg Glu Gln Glu Leu Asp
1               5                   10                  15

Gln His Lys Val Trp Val Gln Gln Ser Ile Arg Asn Val
            20                  25

(2) INFORMATION FOR SEQ ID NO: 15:

(i) SEQUENCE CHARACTERISTICS:
        (A) LENGTH: 29 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO: 15:

Leu Lys Ala Glu Ile Glu Asp Leu Glu Leu Lys Glu Arg Glu Leu Asp
1               5                   10                  15

Gln Gln Lys Leu Trp Leu Gln Gln Ser Ile Lys Asn Val
            20                  25

(2) INFORMATION FOR SEQ ID NO: 16:

(i) SEQUENCE CHARACTERISTICS:
        (A) LENGTH: 21 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO: 16:

Asn Phe Gln Ile Ser Leu Lys Ser Lys Gln Gly Pro Ile Asp Val Phe
 1               5                  10                  15

Leu Cys Pro Glu Glu
            20

(2) INFORMATION FOR SEQ ID NO: 17:

(i) SEQUENCE CHARACTERISTICS:
        (A) LENGTH: 21 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO: 17:

Asn Leu Gln Ile Tyr Leu Lys Ser Thr Gln Gly Pro Ile Glu Val Tyr
 1               5                  10                  15

Leu Cys Pro Glu Glu
            20

(2) INFORMATION FOR SEQ ID NO: 18:

(i) SEQUENCE CHARACTERISTICS:
        (A) LENGTH: 21 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO: 18:

Ser Leu Gln Ile His Leu Ala Ser Ile Gln Gly Pro Ile Glu Val Tyr
 1               5                  10                  15

Leu Cys Pro Glu Glu
            20

(2) INFORMATION FOR SEQ ID NO: 19:

(i) SEQUENCE CHARACTERISTICS:
        (A) LENGTH: 21 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO: 19:

Lys Tyr Gln Ile His Leu Lys Ser Val Ser Gly Pro Ile Glu Val Leu
 1               5                  10                  15

Leu Val Asn Lys Glu
            20

(2) INFORMATION FOR SEQ ID NO: 20:

(i) SEQUENCE CHARACTERISTICS:
        (A) LENGTH: 21 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO: 20:

Lys Tyr Gln Ile Asn Leu Lys Ser His Ser Gly Pro Ile His Val Leu
1               5                   10                  15

Leu Ile Asn Lys Glu
            20

(2) INFORMATION FOR SEQ ID NO: 21:

(i) SEQUENCE CHARACTERISTICS:
        (A) LENGTH: 19 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO: 21:

Ala Leu Asp Tyr His Phe Gly Leu Glu Glu Gly Glu Gly Ile Arg Asp
1               5                   10                  15

Leu Phe Asp (2) INFORMATION FOR SEQ ID NO: 22:

(i) SEQUENCE CHARACTERISTICS:
        (A) LENGTH: 19 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO: 22:

Gln Asp Asp Tyr Leu Trp Gly Leu Glu Ala Gly Glu Gly Ile Ser Asp
1               5                   10                  15

Leu Phe Asp (2) INFORMATION FOR SEQ ID NO: 23:

(i) SEQUENCE CHARACTERISTICS:
        (A) LENGTH: 19 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO: 23:

Gln Glu Asp Tyr Leu Leu Ser Leu Gly Glu Glu Gly Ile Ser Asp
1               5                   10                  15

Leu Phe Asp (2) INFORMATION FOR SEQ ID NO: 24:

(i) SEQUENCE CHARACTERISTICS:
        (A) LENGTH: 19 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO: 24:

Asp His Asp Tyr Ile Tyr Asn Leu Asp Glu Ser Glu Gly Val Cys Asp
1               5                   10                  15

Leu Phe Asp

```
(2) INFORMATION FOR SEQ ID NO: 25:

(i) SEQUENCE CHARACTERISTICS:
        (A) LENGTH: 18 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO: 25:

Asp Asp Tyr Asn Phe Asn Leu Asp Asp Asn Glu Gly Val Cys Asp Leu
1               5                   10                  15

Phe Asp
```

US 6,448,376 B1

TRANSCRIPTION FACTOR-E2F-5

This invention relates to a novel transcription factor and to its production and uses.

The molecular events that occur during the cell cycle need to be integrated with the transcription apparatus so that gene expression can be synchronised with cell cycle progression.

Recently, a transcription factor called E2F (or DRTF1) has been identified and shown to bind to pRb, the protein product of the retinoblastoma susceptibility gene, an anti-oncogene or tumour suppressor gene (see for example Wagner and Green, Nature 352, 189–190, 1991). It is widely believed that the cellular transcription factor E2F functions as a key component in cell cycle control because it associates with important cell cycle regulating proteins, such as the retinoblastoma gene product (pRb), p107, cyclins and cyclin-dependent kinases, and furthermore its transcriptional activity is modulated by certain viral oncoproteins, such as adenovirus Ela, SV40 large T antigen, and the human papilloma virus E7 protein.

It is believed that the transcription factor E2F (or DRTF1) plays an important role in integrating cell cycle events with the transcription apparatus because, during cell cycle progression in mammalian cells, it undergoes a series of periodic interactions with molecules that are known to be important regulators of cellular proliferation. For example, the retinoblastoma tumour suppressor gene product (pRb), which negatively regulates progression from G1 into S phase. and is frequently modified in tumour cells, binds to E2F. Similarly, the pRb-related protein p107 occurs predominantly in an S phase complex with E2F. Both pRb and p107 repress the transcriptional activity of E2F, which is likely to be fundamentally important for regulating cellular proliferation because E2F binding sites occur in the control regions of a variety of genes that are involved with proliferation, such as c-myc and $p34^{cdc2}$. Furthermore, mutant Rb proteins, encoded by alleles isolated from tumour cells, fail to bind to E2F, and hence are unable to interfere with E2F site-dependent transcriptional activation. Another important feature of E2F is that certain viral oncoproteins, such as adenovirus Ela, SV40 large T antigen and human papilloma virus E7, modulate its activity by sequestering pRb and p107 from the inactive transcription factor. This effect requires regions in these viral proteins that are necessary for transformation of tissue culture cells and hence to overcome growth control. Thus, the ability of these oncoproteins to regulate E2F may be the means by which they over-ride the normal mechanisms of cellular growth control and, conversely, transcriptional repression by pRb may be the basis of pRb-mediated negative growth control.

A potential mechanism for integrating the transcription-regulating properties of pRb and p107 with other cell cycle events was suggested by the identification of cyclin A and the cdc2-related cyclin-dependent kinase $p33^{cdk2}$ in the E2F complex. Cyclin A is necessary for progression through S phase, a function that could perhaps be mediated through its ability to recruit the cyclin-dependent kinase $p33^{cdk2}$ to E2F. Taken together these data suggest that E2F is a transcription factor whose primary role may be to relay cell cycle events to the transcription apparatus via molecules such a pRb, p107, cyclins and cdks, thus ensuring that gene expression is synchronised and integrated with cell cycle progression.

More recently, a transcription factor with the properties of E2F has been cloned and sequenced (Helin et al, Cell 70 (1992), 337–350 and Kaelin et al, Cell 70 (1992), 351–364).

SUMMARY OF THE INVENTION

We have now surprisingly found a further two new proteins which appear to be new members of the E2F gene family, which we have called E2F-5. The cDNA sequence of human E2F-5 is presented in FIG. 1A, as is the amino acid sequence of this protein. The corresponding sequences for murine E2F-5 appear in FIG. 9A. These new proteins are referred to as E2F-5 and this nomenclature will be used in this specification.

(B) Schematic representation of E2F-5 in comparison with E2F-1 and E2F-4. The borders of the conserved domains are indicated by amino acid number. SS in E2F-4 indicates the serine-rich motif.

Figure 2:
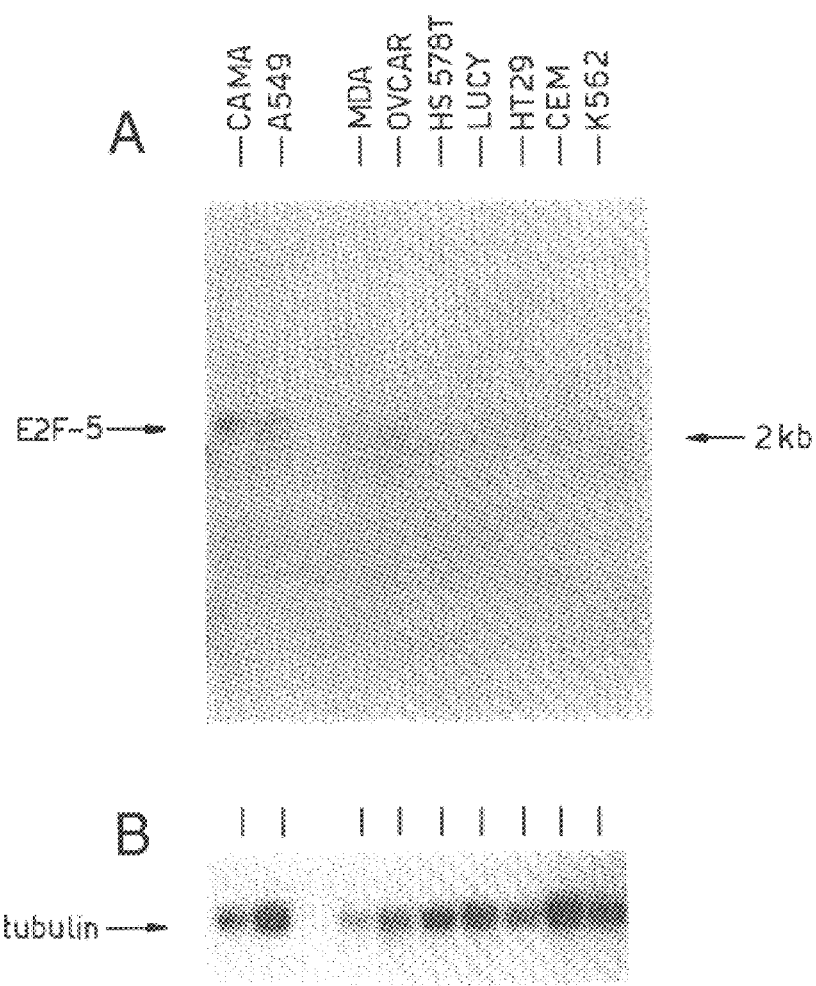

FIG. 2 Expression pattern of E2F-5 in human cell lines.

(A) Northern blot containing total cytoplasmic RNA from the indicated human cell lines was hybridized to a human E2F-5 cDNA probe. RNAs from the follow human cell lines was used: CAMA, human breast carcinoma; A549, lung carcinoma; MDA, MDA-MD157 breast carcinoma; OVCAR, ovarium carcinoma; HS 578T, breast carcinoma; LUCY, ovarium carcinoma; HT29, colon carcinoma: CEM, T-cell leukemia; K562, erythroleukemia. (B) The same filter hybridized with a rar α-tubulin probe.

Figure 3:
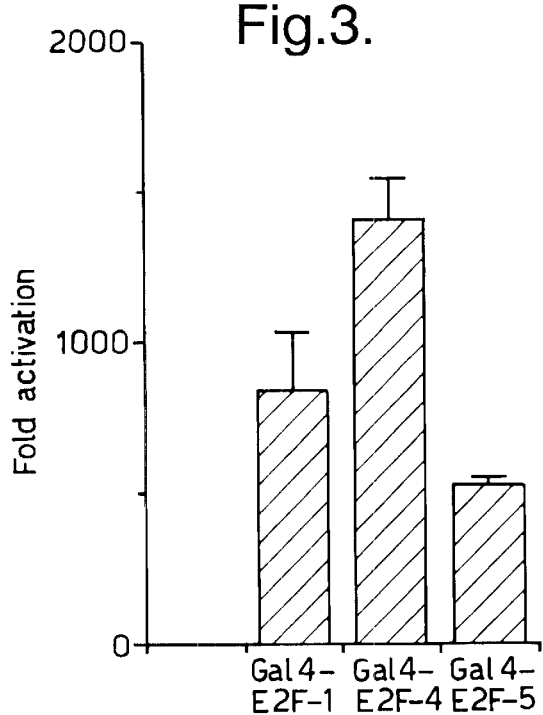

FIG. 3. E2F-5 has a corboxyl-terminal transactivation domain.

U-2 OS cells were transfected with a CAT reporter plasmid harboring upstream Gal4 sites (5 μg) in the presence or absence of Gal-4-E2F expression vectors (1 μg) and 0.2 μg pRSV-Luciferase as an internal control. CAT activiry was normalize to the luciferase activity for each sample. CAT activity was assayed two days post transfection . The fold activation of Gal4-E2F over CAT reporter gene alone is represented. Data are representative for at least three independent experiments done in duplicate.

Figure 4:
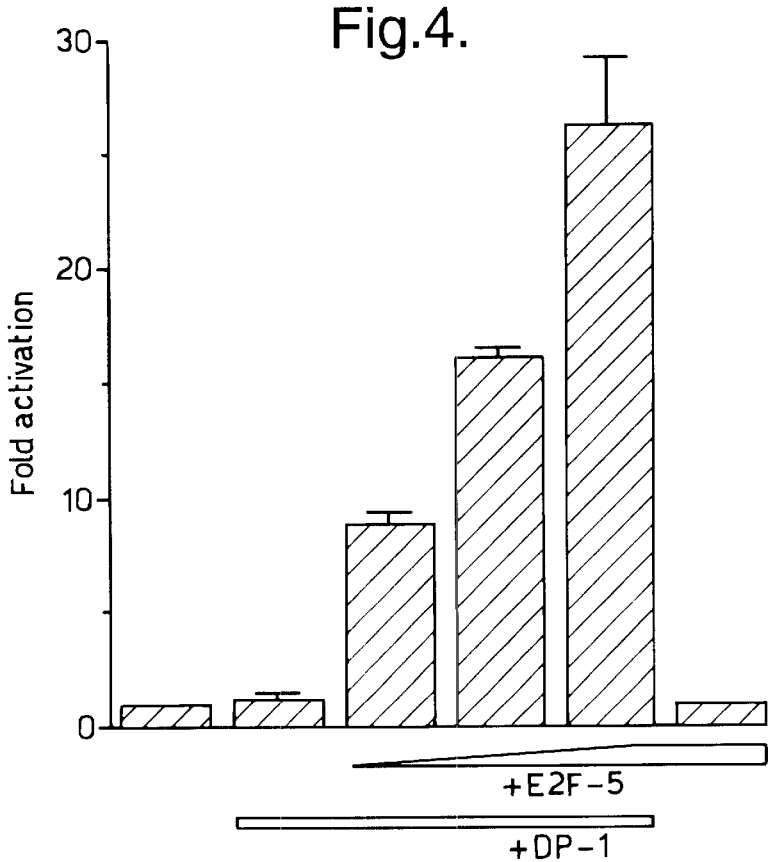

FIG. 4. E2F-5 and DP-1 cooperate in transactivation.

U2-OS osteosarcoma cells were transfected with increasing amounts of pJ3-E2F-5 expression vector (1, 2, or 5 μg) together with 100 ng pCMV-DP-1, as indicated. In each transfection 2 μg reporter construct ($E2F_4$-CAT) and 0.2 μg pRSV-Luciferase was added. CAT activity was normalized to the luciferase activity for each sample. Data are representative for at least three independent experiments done in duplicate.

Figure 5:
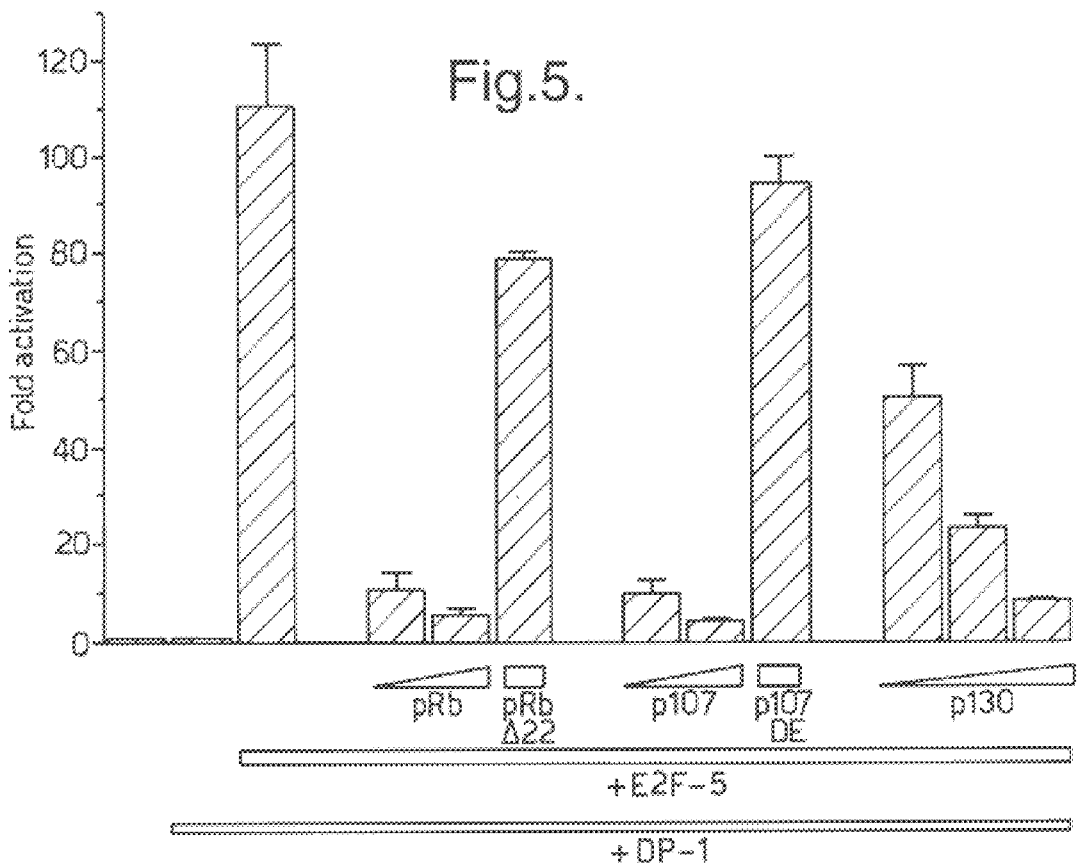

FIG. 5. Inhibition of E2F-5 transactivation by pocket proteins.

U2-OS cells were transfected with 5 μg pJ3E2F-5 and 100 ng pCMV-DP-1 in combination with pCMV-Rb (50 and 100 ng), pCMV-RbΔ22 (100 ng), pCMV-p107 (50 and 100 ng), pCMVp107DE (100 ng) or pCMV-HA-p130 (50, 100 and 500 ng). Together with the expression plasmids, the cells were transfected with 2 μg $E2F_4$-CAT and 0.2 μg pRSV-Luciferase. CAT activity was normalized to the luciferase internal control. Fold activation was calculated relative to the basal level of $E2F_4$-CAT which was set to unity (1.0). Data are representative for at least three independent experiments done in duplicate.

Figure 6:
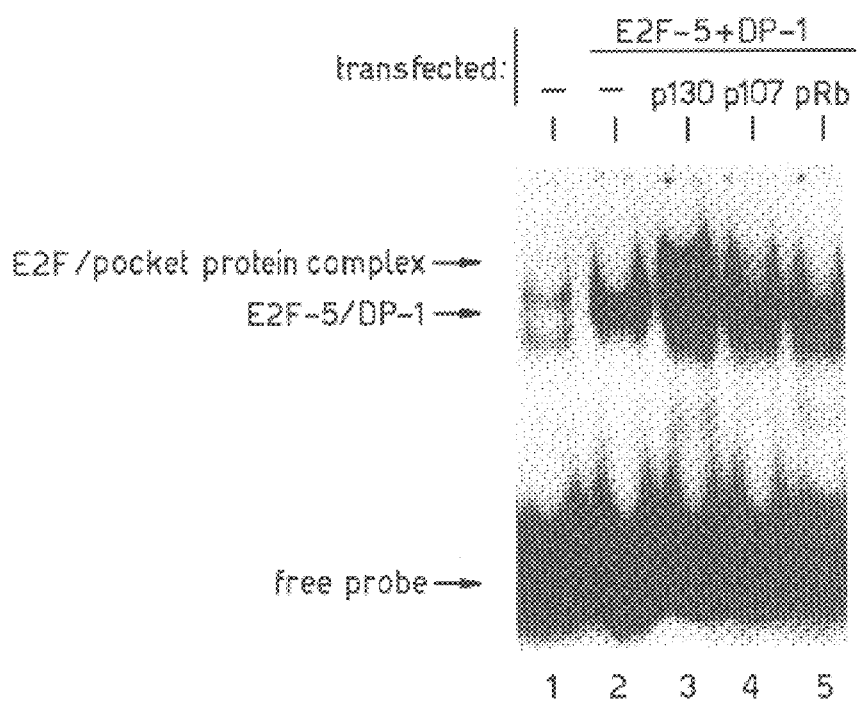

FIG. 6. E2F containing complexes in transiently transfected U2-OS cells.

U2-OS osteosarcoma cells were transiently transfected with E2F-5 and DP-1 expression vectors in the presence or absence of pRb- p107 or p130 expression vectors as indicated. After two days, whole cell extracts were prepared and incubated with a [$^{12}$P]-labeled oligonucleotide containing a consensus E2F DNA binding site and subjected to gel electrophoresis. The position of free probe, E2F-5/DP-1 DNA complex and E2F-5/pocket protein complex is indicated.

Figure 7:
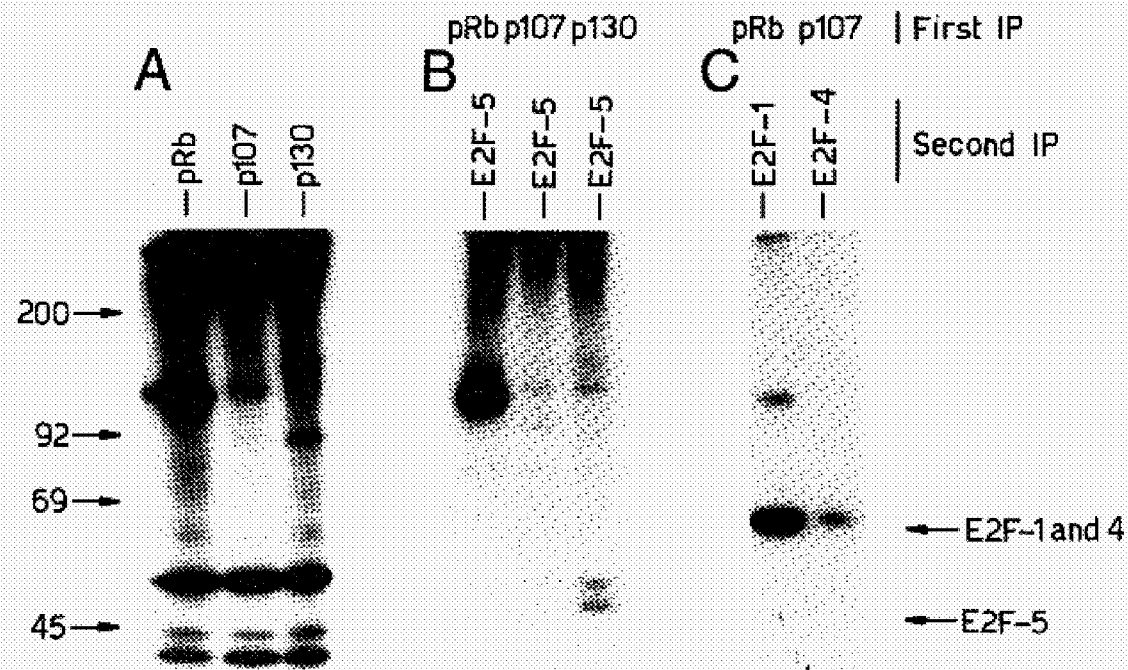

FIG. 7. E2F-5 preferentially interacts with p130 in vivo.

Human CAMA breast carcinoma cells were labeled with [$^{32}$P]-orthophosphate and non-ionic detergent lysates were subjected to sequential immunoprecipitation. In a first immunoprecipitation lysates were incubated with pRb, p107 or p130 antibody as indicated. Panel A shows the first immunoprecipitations with pRb- p107 and p130-specific antibodies from CAMA cells. The pRb-, p107 and p130-associated proteins were released from the immunoprecipitated pocket proteins by boiling in SDS-containing buffer and re-immunoprecipitated with e2F-5-specific antiserum (panel B). As a control, proteins released from pRb- and p107 immunoprecipitates were re-immunoprecipitated with anti E2F-1 (KH20) or E2F-4 (RK13) antibody (panel C). Immunoprecipitated proteins were separated on 7.5% SDS-polyacrylamide gels, the gels were dried and proteins were detected by autoradiography.

FIG. 8

Strategy for isolating murine E2F-5 (SEQ ID NO:3)

The 'bait', LEXA DP-1, was used to screen a 14.5 d.p.c. mouse embryo activation-domain tagged cDNA library.

FIG. 9

Sequence and comparison of murine E2F-5 with other members of the E2F family.

(a) Nucleotide sequence together with predicted amino acid residue sequence of E2-F5. (SEQ ID NOs: 3 and 4, respectively)

(b) Diagrammatic representation and comparison of E2F-5 (middle) with E2F-1 (top) and E2F-4 (bottom). Percentage identities at the level of protein sequence are indicated between E2F-5 and E2F-1, and E2F-5 and E2F-4. Domains shared between E2F family members are indicated (Lees et al., 1993).

(c) Comparison of amino acid residue sequence in the conserved domains within the E2F; family members.

(SEQ ID NOs: 5–10) The highlighted residues are common to all family members, whereas boxed residues are common to E2F-4 and E2F-5. Bold residues in the leucine zip region indicate hydrophobics in a heptad repeat. Residues in the DEF box region which are shared between E2F family member and DP-1 are indicated by the lines. (SEQ ID NOs:11–25)

DNA Binding/Dimerization E2F-1 (SEQ ID NO:5)
DNA Binding/Dimerization E2F-2 (SEQ ID NO:6)
DNA Binding/Dimerization E2F-3 (SEQ ID NO:7)
DNA Binding/Dimerization E2F-4 (SEQ ID NO:8)
DNA Binding/Dimerization E2F-5 (SEQ ID NO:9)
DNA Binding/Dimerization DP-1 (SEQ ID NO:10)
Leucine Zip E2F-1 (SEQ ID NO:11)
Leucine Zip E2F-2 (SEQ ID NO:12)
Leucine Zip E2F-3 (SEQ ID NO:13)
Leucine Zip E2F-4 (SEQ ID NO:14)
Leucine Zip E2F-5 (SEQ ID NO:15)
Marked Box E2F-1 (SEQ ID NO:16)
Marked Box E2F-2 (SEQ ID NO:17)
Marked Box E2F-3 (SEQ ID NO:18)
Marked Box E2F-4 (SEQ ID NO:19)
Marked Box E2F-5 (SEQ ID NO:20)
Pocket Protein Binding E2F-1 (SEQ ID NO:21)
Pocket Protein Binding E2F-2 (SEQ ID NO:22)
Pocket Protein Binding E2F-3 (SEQ ID NO:23)
Pocket Protein Binding E2F-4 (SEQ ID NO:24)
Pocket Protein Binding E2F-5 (SEQ ID NO:25)

FIG. 10

Activation of E2F site-dependent transcription by E2F-5 and DP-1 in yeast.

(a) Summary of reporter and effector constructs.

(b) The indicated E2F-5 and DP-1 expression vectors were transformed into yeast either alone (lanes 2 and 3) or together (lane 4) and the activity of p4xWT CYC1, which carries four wild-type E2F sites, assessed. In parallel experiments, the activity of p4xMT CYC1 was not affected in any of the conditions. The data presented were derived from triplicate readings.

FIG. 11

Transcriptional activation by E2F-5 in yeast.

(a) Summary of reporter and effector constructs (b) The transcription activity of either pLEX.E2F-1 (track 2) or pLEX.E2F-5 (track 3) was assessed in yeast by assaying the activity of pLexA-CYC1-lacZ. The data presented were derived from triplicate readings.

FIG. 12

Pocket protein regulation E2F-5.

(a) Summary of reporter and effector constructs.

(b) The transcriptional activity of Gal-E2F-5 (track 2) was assessed in the presence of wild-type pRb (track 3), pRbΔ22 (track 4), p107 (track 5) and p107AS (track 6). For comparison, similar treatments were performed with pG4 (tracks 7 to 10). The data presented were derived from triplicate readings.

FIG. 13

E2F-5 is a physiological DNA binding component of DRTF1/E2F in F9 EC cells.

Two types of antisera raised against distinct peptides from different regions within E2F-5 were assessed for their effect on F9 EC cell DRTF1/E2F DNA binding activity. The anti-E2F-5 sera, anti-peptide 1 (tracks 5 to 8) and anti-peptide 2 (track 9 to 12) were assessed in the presence of either the homolgous (+; tracks 5, 7, 9 and 11) or an unrelated (−; tracks 6, 8, 10 and 12) peptide. For comparison, the effect of anti-DP-1(24) (tracks 1 to 4) in the presence of either the homologous (tracks 1 and 3) or an unrelated peptide (tracks 2 and 4) was assessed. Each pair or tracks (+ together with −) represents treatment with a different preparation of antiserum. The DRTF1/E2F b/c DNA binding complexes (La Thangue et al., 1990) are indicated.

FIG. 14

DNA binding properties of E2F-5.

E2F-5, E2F-1 and DP-1 were expressed as GST fusion proteins, purified and their DNA binding activity assayed by gel retardation. Either E2F-1 or E2F-5 were assayed alone (tracks 1 and 2, and 5, 6, and 7 respectively) or together with a constant concentration of DP-1 (tracks 3 and 4, and 8,9 and 10). Track 11 shows the probe alone. The amount of proteins added for E2F-1 was approximately 50 ng (tracks 1 and 3) or 100 ng (tracks 2 and 4), for E2F-5 25 ng (tracks 5 and 8), 50 ng (tracks 6 and 9) or 100 ng (tracks 7 and 10), and for DP-1 50 ng throughout.

FIG. 15

Levels of E2F-5 RNA.

The levels of E2F-5 RNA were compared to E2F-1 in the indicated cell lines. The level of GAPDH RNA was assessed as an internal control.

It has been found that E2F-S is one of a family of related transcription factor components. Members of this family are believed to interact with DP proteins to form a series of transcription factors. DP proteins (or polypeptides) include DP-1, DP-2 and DP-3 although the first of these will usually be contemplated in preference to the others.

Figure 9:
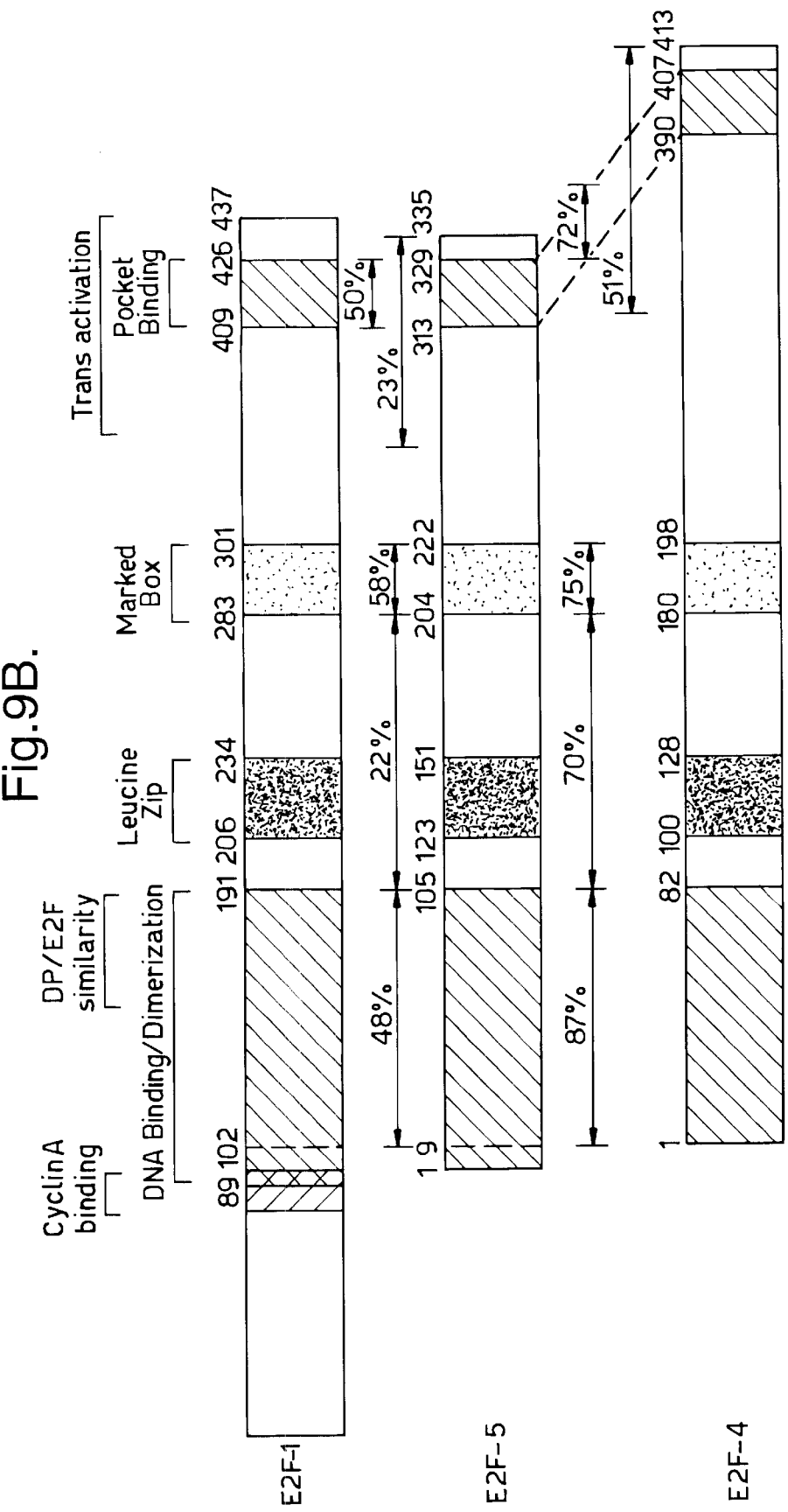

The invention in a first aspect provides a protein as shown in FIG. 1A or 9A, homologues thereof, and fragments of the sequence and their homologues, which can function as a mammalian transcription factor. In particular, the invention provides a polypeptide (preferably in substantially isolated form) comprising:

(a) E2F-5;

(b) the protein of FIG. 1A or 9A;

(c) a mutant, allelic variant or species homologue of (a) or (b);

(d) a protein at least 70% homologous to (a) or (b);

(e) a fragment of any one of (a) to (d) capable of forming a complex with a DP protein, pRb, p107 and/or p130; or (f) a fragment of any of (a) to (e) of at least 15 amino acids long.

All polypeptides within this definition are referred to below as polypeptide(s) according to the invention.

The proteins pRb, p107, DP proteins and p130 are referred to herein as complexing proteins or "complexors" as they may form a complex with the proteins of the invention. Under certain conditions E2F-5 may only bind weakly to pRb.

A polypeptide of the invention will be in substantially isolated form if it is in a form in which it is free of other polypeptides with which it may be associated in its natural environment (eg the body). It will be understood that the polypeptide may be mixed with carriers or diluents which will not interfere with the intended purpose of the polypeptide and yet still be regarded as substantially isolated.

The polypeptide of the invention may also be in a substantially purified form, in which case it will generally comprise the polypeptide in a preparation in which more than 90%, eg. 95%, 98% or 99% of the polypeptide in the preparation is a polypeptide of the invention.

Mutant polypeptides will possess one or more mutations which are additions, deletions, or substitutions of amino acid residues. Preferably the mutations will not affect, or substantially affect, the structure and/or function and/or properties of the polypeptide. Thus, mutants will suitably possess the ability to be able to complex with DP proteins, pRb, p107 and/or p130. Mutants can either be naturally occurring (that is to say, purified or isolated from a natural source) or synthetic (for example, by performing site-directed mutagenesis on the encoding DNA). It will thus be apparent that polypeptides of the invention can be either naturally occurring or recombinant (that is to say prepared using genetic engineering techniques).

An allelic variant will be a variant which will occur naturally in a human or in an, eg. murine, animal and which will function to regulate gene expression in a substantially similar manner to the protein in FIG. 1A or 9A.

Similarly, a species homologue of the protein will be the equivalent protein which occurs naturally in another species, and which performs the equivalent function in that species to the protein of FIG. 1A or 9A. Within any one species, a homologue may exist as several allelic variants, and these will all be considered homologues of the protein. Allelic variants and species homologues can be obtained by following the procedures described herein for the production of the protein of FIG. 1A or 9A and performing such procedures on a suitable cell source, eg from human or a rodent, carrying an allelic variant or another species. Since the protein may be evolutionarily conserved it will also be possible to use a polynucleotide of the invention to probe libraries made from human, rodent or other cells in order to obtain clones encoding the allelic or species variants. The clones can be manipulated by conventional techniques to identify a polypeptide of the invention which can then be produced by recombinant or synthetic techniques known per se. Preferred species homologues include mammalian or amphibian species homologues.

A protein at least 70% homologous to that in FIG. 1A or 9A is included in the invention, as are proteins at least 80 or 90% and more preferably at least 95% homologous to the protein shown in these Figures. This will generally be over a region of at least 20, preferably at least 30, for instance at least 40, 60 or 100 or more contiguous amino acids. Methods of measuring protein homology are well known in the art and it will be understood by those of skill in the art that in the present context. Homology is usually calculated on the basis of amino acid identity (sometimes referred to as "hard homology").

Generally, fragments of the polypeptide in FIG. 1A or 9A or its allelic variants or species homologues thereof capable of forming a complex with the complexors will be at least 10, preferably at least 15, for example at least 20, 25, 30, 40, 50 or 60 amino acids in length.

It will be possible to determine whether fragments form a complex with the complex of proteins by providing the complexor protein and the fragment under conditions in which they normally form a trans-activating transcription factor, and determining whether or not a complex has formed. The determination may be made by, for example, measuring the ability of the complex to bind an E2F binding site in vitro, or alternatively determining the molecular weight of the putative complex by methods such as SDS-PAGE.

Preferred fragments include those which are capable of forming a trans-activation complex with DP-1 or other complexors. The examples herein describe a number of methods to analyse the function of the protein and these may be adapted to assess whether or not a polypeptide is capable of forming a trans-activation complex with the DP-1 protein. For example, the polypeptide can be added to the complexor in the presence of a reporter gene construct adapted to be activated by the DP-1/E2F-5 complex (for example, see FIG. 10 of WO-A-94/10307 in the name of the Medical Research Council). Such an experiment can determine whether the polypeptide fragment has the necessary activity.

A polypeptide of the invention may be labelled with a revealing or detectable label. The (revealing) label may be any suitable label which allows the polypeptide to be detected. Suitable labels include radioisotopes, e.g. $^{125}$I, enzymes, antibodies and linkers such as biotin. Labelled polypeptides of the invention may be used in diagnostic procedures such as immunoassays in order to determine the amount of E2F-5 protein in a sample.

A polypeptide or labelled polypeptide according to the invention may also be fixed to a solid phase, for example the wall of an immunoassay dish.

A second aspect of the invention relates to a polynucleotide which comprises:

(a) a sequence of nucleotides shown in FIG. 1A or 9A;

(b) a sequence complementary to (a);

(c) a sequence capable of selectively hybridising to a sequence in either (a) or (b);

(d) a sequence encoding a polypeptide as defined in the first aspect; or (e) a fragment of any of the sequences in (a) to (d).

The present invention thus provides a polynucleotide, suitably in substantially isolated or purified form, which comprises a contiguous sequence of nucleotides which is capable of selectively hybridizing to the sequence of FIG. 1A or 9A or to a complementary sequence.

Polynucleotides of the invention include a DNA sequence in FIG. 1A or 9A and fragments thereof capable of selectively hybridizing to the sequence of FIG. 1A or 9A. A further embodiment of the invention provides a DNA coding for the protein in FIG. 1A or 9A or a fragment thereof.

The polynucleotide may also comprise RNA. It may also be a polynucleotide which includes within it synthetic or modified nucleotides. A number of different types of modification to oligonucleotides are known in the art. These include methylphosphonate and phosphorothionate backbones, addition of acridine or polylysine chains at the 3' and/or 5' ends of the molecule. For the purposes of the present invention, it is to be understood that the oligonucleotides described herein may be modified by any method available in the art. Such modifications may be carried out in order to enhance the in vivo activity or lifespan of oligonucleotides of the invention used in methods of therapy.

A polynucleotide capable of selectively hybridizing to the DNA of FIG. 1A or 9A will be generally at least 70%, preferably at least 80 or 90% and optimally at least 95% homologous to the DNA of FIG. 1A or 9A over a region of at least 20, preferably at least 30, for instance at least 40, 60 or 100 or more contiguous nucleotides. These polynucleotides are within the invention.

A polynucleotide of the invention will be in substantially isolated form if it is in a form in which it is free of other polynucleotides with which it may be associated in its natural environment (usually the body). It will be understood that the polynucleotide may be mixed with carriers or diluents which will not interfere with the intended purpose of the polynucleotide and it may still be regarded as substantially isolated.

A polynucleotide according to the invention may be used to produce a primer, e.g. a PCR primer, a probe e.g. labelled with a revealing or detectable label by conventional means using radioactive or non-radioactive labels, or the polynucleotide may be cloned into a vector. Such primers, probes and other fragments of the DNA of FIG. 1A or 9A will be at least 15, preferably at least 20, for example at least 25, 30 or 40 nucleotides in length, and are also encompassed within the invention.

Polynucleotides, such as a DNA polynucleotides according to the invention may be produced recombinantly, synthetically, or by any means available to those of skill in the art. It may be also cloned by reference to the techniques disclosed herein.

The invention includes a double stranded polynucleotide comprising a polynucleotide according to the invention and its complement.

A third aspect of the invention relates to an (eg. expression) vector suitable for the replication and expression of a polynucleotide, in particular a DNA or RNA polynucleotide, according to the invention. The vectors may be, for example, plasmid, virus or phage vectors provided with an origin of replication, optionally a promoter for the expression of the polynucleotide and optionally a regulator of the promoter. The vector may contain one or more selectable marker genes, for example an ampicillin resistance gene in the case of a bacterial plasmid or a neomycin resistance gene for a mammalian vector. The vector may be used in vitro, for example for the production of RNA or used to transfect or transform a host cell. The vector may also be adapted to be used in vivo, for example in a method of gene therapy.

Vectors of the third aspect are preferably recombinant replicable vectors. The vector may thus be used to replicate the DNA. Preferably, the DNA in the vector is operably linked to a control sequence which is capable of providing for the expression of the coding sequence by a host cell. The term "operably linked" refers to a juxtaposition wherein the components described are in a relationship permitting them to function in their intended manner. A control sequence "operably linked" to a coding sequence is ligated in such a way that expression of the coding sequence is achieved under condition compatible with the control sequences. Such vectors may be transformed or transfected into a suitable host cell to provide for expression of a polypeptide of the invention.

A fourth aspect of the invention thus relates to host cells transformed or transfected with the vectors of the third aspect. This may allow for the replication and expression of a polynucleotide according to the invention, including the sequence of FIG. 1A or 9A or the open reading frame thereof. The cells will be chosen to be compatible with the vector and may for example be bacterial, yeast, insect or mammalian.

A polynucleotide according to the invention may also be inserted into the vectors described above in an antisense orientation in order to provide for the production of antisense RNA. Antisense RNA or other antisense polynucleotides may also be produced by synthetic means. Such antisense polynucleotides may be used in a method of controlling the levels of the E2F-5 protein in a cell. Such a method may include introducing into the cell the antisense polynucleotide in an amount effective to inhibit or reduce the level of translation of the E2F-5 mRNA into protein. The cell may be a cell which is proliferating in an uncontrolled manner such as a tumour cell.

Thus, in a fifth aspect the invention provides a process for preparing a polypeptide according to the invention which comprises cultivating a host cell transformed or transfected with an (expression) vector of the third aspect under conditions providing for expression (by the vector) of a coding sequence encoding the polypeptide, and recovering the expressed polypeptide.

The invention in a sixth aspect also provides (monoclonal or polyclonal) antibodies specific for a polypeptide according to the invention. Antibodies of the invention include fragments, thereof as well as mutants that retain the antibody's binding activity. The invention further provides a process for the production of monoclonal or polyclonal antibodies to a polypeptide of the invention. Monoclonal antibodies may be prepared by conventional hybridoma technology using the proteins or peptide fragments thereof as an immunogen. Polyclonal antibodies may also be prepared by conventional means which comprise inoculating a host animal, for example a rat or a rabbit, with a polypeptide of the invention and recovering immune serum.

Fragments of monoclonal antibodies which can retain their antigen binding activity, such Fv, F(ab') and F(ab$_2$)' fragments are included in this aspect of the invention. In addition, monoclonal antibodies according to the invention may be analyzed (eg. by DNA sequence analysis of the genes expressing such antibodies) and humanized antibody with complementarity determining regions of an antibody according to the invention may be made, for example in accordance with the methods disclosed in EP-A-0239400 (Winter).

The present invention further provides compositions comprising the antibody or fragment thereof of the invention together with a carrier or diluent. Such compositions include pharmaceutical compositions in which case the carrier or diluent will be pharmaceutically acceptable.

Polypeptides of the invention can be present in compositions together with a carrier or diluent. These compositions include pharmaceutical compositions where the carrier or diluent will be pharmaceutically acceptable.

Pharmaceutically acceptable carriers or diluents include those used in formulations suitable for oral, rectal, nasal, topical (including buccal and sublingual), vaginal or parenteral (including subcutaneous, intramuscular, intravenous, intradermal, intrathecal and epidural) administration. The formulations may conveniently be presented in unit dosage form and may be prepared by any of the methods well known in the art of pharmacy. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

For example, formulations suitable for parenteral administration include aqueous and non-aqueous sterile injection solutions which may contain anti-oxidants. buffers, bacteriostats and solutes which render the formulation isotonic with the blood of the intended recipient; and aqueous and non-aqueous sterile suspensions which may include suspending agents and thickening agents, and liposomes or other microparticulate systems which are designed to target the polypeptide to blood components or one or more organs.

Polypeptides according to the invention, antibodies or fragments thereof to polypeptides according to the invention and the above-mentioned compositions may be used for the treatment, regulation or diagnosis of conditions, including proliferative diseases, in a mammal including man. Such conditions include those associated with abnormal (eg at an unusually high or low level) and/or aberrant (eg due to a mutation in the gene sequence) expression of one or more transcription factors such as the DP or E2F proteins or related family members. The conditions also include those which are brought about by abnormal expression of a gene whose gene product is regulated by the protein of FIG. 1A or 9A. Treatment or regulation of conditions with the above-mentioned peptides, antibodies, fragments thereof and compositions etc. will usually involve administering to a recipient in need of such treatment an effective amount of a polypeptide, antibody, fragment thereof or composition, as appropriate.

The invention also provides antibodies, and fragments thereof, targeted to this region in order to inhibit the activation of transcription factors via the disruption of the formation of the E2F-5-DP protein complex.

The present invention further provides a method of performing an immunoassay for detecting the presence or absence of a polypeptide of the invention in a sample, the method comprising:

(a) providing an antibody according to the invention;
(b) incubating the sample with the antibody under conditions that allow for the formation of an antibody-antigen complex; and
(c) detecting, if present, the antibody-antigen complex.

In another aspect, the invention provides a novel assay for identifying putative chemotherapeutic agents for the treatment of proliferative or viral disease which comprises bringing into contact a DP protein or a derivative thereof, a polypeptide of the invention and a putative chemotherapeutic agent, and measuring the degree of inhibition of formation of the DP/E2F-5 protein complex caused by the agent. It may not be necessary to use complete DP-1 and/or E2F-5 protein in the assay, as long as sufficient of each protein is provided such that under the conditions of the assay in the absence of agent, they form a heterodimer.

The cloning and sequencing of DP-1 (and E2F 1,2 and 3) are known in the art and methods for the recombinant expression and preparation of antibodies to DP-1 can be found in WO-A-94/10307.

Thus, the invention provides a screening method for identifying putative chemotherapeutic agents for the treatment of proliferative disease which comprises:

(A) bringing into contact:
(i) a DP polypeptide;
(ii) a polypeptide of the first aspect, and
(iii) a putative chemotherapeutic agent;
under conditions in which the components (i) and (ii) in the absence of (iii) form a complex; and
(B) measuring the extent to which component (iii) is able to disrupt said complex.

In the assay, any one or more of the three components may be labelled, eg with a radioactive or calorimetric label, to allow measurement of the result of the assay. Putative chemotherapeutic agents include peptides of the invention.

Variants, homologues and fragments of DP proteins are defined in a corresponding manner to the variants, homologues and fragments of the E2F-5 protein.

The complex of (i) and (ii) may be measured, for example, by its ability to bind an E2F DNA binding site in vitro. Alternatively, the assay may be an in vivo assay in which the ability of the complex to activate a promoter comprising an E2F binding site linked to a reporter gene is measured. The in vivo assay may be performed for example by reference to the examples which show such an assay in yeast, insect, amphibian or mammalian cells.

Candidate therapeutic agents which may be measured by the assay include not only polypeptides of the first aspect, but in particular fragments of 10 or more amino acids of:

(a) the protein of FIG. 1A or 9A;
(b) an allelic variant or species homologue thereof; or
(c) a protein at least 70% homologous to (a).

Vectors carrying a polynucleotide according to the invention or a nucleic acid encoding a polypeptide according to the invention may be used in a method of gene therapy. Such gene therapy may be used to treat uncontrolled proliferation of cells, for example a tumour cell. Methods of gene therapy include delivering to a cell in a patient in need of treatment an effective amount of a vector capable of expressing in the cell either an antisense polynucleotide of the invention in order to inhibit or reduce the translation of E2F-5 mRNA into E2F-5 protein or a polypeptide which interferes with the binding of E2F-5 to a DP protein or a related family member.

The vector is suitably a viral vector. The viral vector may be any suitable vector available in the art for targeting tumour cells. For example, Huber et al (Proc. Natl. Acac. Sci. USA (1991) 88, 8039) report the use of amphotrophic retroviruses for the transformation of hepatoma, breast, colon or skin cells. Culver et al (Science (1992) 256; 1550–1552) also describe the use of retroviral vectors in virus-directed enzyme prodrug therapy, as do Ram et al (Cancer Research (1993) 53; 83–88). Englehardt et al (Nature Genetics (1993) 4; 27–34 describe the use of adenovirus based vectors in the delivery of the cystic fibrosis transmembrane conductance product (CFTR) into cells.

The invention contemplates a number of assays. Broadly, these can be classified as follows.

1. Conducting an assay to find an inhibitor of E2F-5 trans-activation (that is to say, inhibition of activation of transcription). This inhibitor may therefore inhibit binding of E2F-5 to DNA (usually at the E2F binding site). Potentially suitable inhibitors are proteins, and may have a similar or same effect as p107. Thus suitable inhibitory molecules may comprise fragments, mutants, allelic variants, or species homologues of p107 in the same manner as defined for proteins of the first aspect.

2. Assaying for inhibitors of (hetero)dimerisation. Such inhibitors may prevent dimerisation of E2F-5 (or a polypeptide of the first aspect) with a complexor, for example a DP protein, such as DP-1. Of course the inhibitor can be a fragment, mutant, allelic variant or species homologue of a DP protein in a similar manner as defined for the proteins of the first aspect.

3. A third category of assay is to find inhibitors of phosphorylation. It is thought that E2F-5 (and other proteins of the first aspect) might be activated by phosphorylation. Therefore, an inhibitor of phosphorylation is likely to inhibit E2F-5 trans-activation properties (and may therefore, ultimately have the same effect as the inhibitors found in either of the two previous assays). Phosphorylation is by cdk's and so an inhibitor of this phosphorylation is one that is contemplated by such assays.

The invention contemplates a number of therapeutic uses. For example, gene therapy using a nucleic acid a sequence that is antisense to E2F-5. Molecules that can bind to a DP-1 protein and thereby form an inactive complex with the DP protein are additionally contemplated. Suitable molecules include those of the first aspect apart from E2F-5 itself. Such molecules may be mutants of E2F-5, and are often referred to as dominant negative molecules in the art.

The invention contemplates the treatment or prophylaxis of diseases that are based on the uncontrolled proliferation of cells, or where uncontrolled proliferation is an important or essential pathological aspect of the disease. This includes cancer, viral disease, self proliferation itself as well as auto immune diseases such psoriasis. One may also wish to temporarily inhibit the growth of dividing cells, for example hematopoietic stem cells and/or bone marrow cells. In these aspects one is generally seeking to prevent, inhibit or interfere with the activity of E2F-5.

In contrast some diseases and conditions can be treated by increasing E2F-5 expression, for example by promoting or inducing overexpression. This preferably results in apoptosis, sometimes known as programmed cell death. Overexpression of the E2F-5 protein can result in death of the cell, and therefore this aspect can also be used in the treatment of cancer. One aim is therefore to increase the activity of E2F-5. Similar uses are known for E2F-1 (Qin et al, PNAS USA 91 (in press)).

It should be borne in mind that the E2F-5 gene might be mutated in tumour cells. In that event, the mutated gene could be used in diagnosis of a condition resulting from the mutation. It also lends itself to treatment via the mutated gene.

The following two Examples describe the isolation and characterization of the novel protein and DNA of the invention from human and murine sources, respectively. However, other e.g. mammalian sources are within the scope of the present invention and other mammalian homologues of the protein may be isolated in an analogous manner. The Examples are presented here by way of illustration and are not to be construed as limiting on the invention.

EXAMPLE 1

SUMMARY

E2F DNA binding sites are found in a number of genes whose expression is tightly regulated during the cell cycle. The activity of E2F transcription factors is regulated by association with specific repressor molecules that can bind and inhibit the E2F transactivation domain. For E2F-1, 2 and 3 the repressor is the product of the retinoblastoma gene, pRb. E2F-4 interacts with pRb-related p107 and not with pRb itself. Recently, a cDNA encoding a third member of the retinoblastoma gene family, p130, was isolated. p130 also interacts with E2F DNA binding activity, primarily in the $G_0$ phase of cell cycle. We report here the cloning of a fifth member of the E2F gene family. The human E2F-5 cDNA encodes a 346-amino acid protein with a predicted molecular mass of 38 kDa. E2F-5 is more closely related to E2F-4 (78% similarity) than to E2F-1 (57% similarity). E2F-5 resembles the other E2Fs in that it binds to a consensus E2F site in a cooperative fashion with DP-1. Using a specific E2F-5 antiserum, we show that under physiological conditions E2F-5 interacts preferentially with p130.

Introduction

E2F is the name given to a group of heterodimeric transcription factors that are composed of an E2F-like and a DP-like subunit [27]. E2F DNA binding sites are present in the promoters of a number of genes whose expression is regulated during the cell cycle and evidence exists to indicate that the presence of these E2F sites contributes to the cell cycle-regulated expression of these genes [13, 28, 38].

E2F DNA binding activity has been found in complex with the retinoblastoma protein (pRb) and the pRb-related p107 and p130 [6, 10, 29, 37]. This group of proteins shares a conserved motif, the "pocket", that is involved in binding to both cellular and viral proteins. For this reason, the group of pRb-like proteins is collectively known as the pocket protein family. Complexes between E2F and the various pocket proteins are likely to have different functions in cell cycle regulation as their appearance differs during the cell cycle. E2F in complex with pRb is found mostly in $G_1$ phase of the cell cycle [5–7, 11]. In contrast, complexes between p107 and E2F persist during the cell cycle, but their composition is variable. In $G_1$, apart from E2F and p107, cyclin E and cdk2 are present. In S phase, cyclin E is replaced by cyclin A in the E2F/p107 complex [29, 37]. The functional significance of the presence of these cyclin/cdk complexes in the p107/E2F complex is not clear at present. In quiescent cells, a complex between E2F and p130 is the most prominent E2F DNA binding species. This complex disappears as cells emerge from quiescence, suggesting a role for p130-interacting E2F activity in cell cycle entry [10].

The ability of E2F to activate transcription is regulated by complex formation with the pocket proteins. Complex formation between E2F and pRb is subject to regulation by phosphorylation. Only the hypophosphorylated species of pRb interact with E2F, indicating. that the phosphorylation of pRb by cyclin/cdk complexes controls the interaction between E2F and pRb during the cell cycle [5–7, 11].

The crucial role of E2F transcription factors in cell cycle regulation is emphasized by the finding that enforced expression of E2F DNA binding activity causes cells to progress from $G_1$ into S and $G_2$/M phases of the cell cycle

[3] and E2F can stimulate quiescent cells to initiate DNA synthesis [23]. Importantly, over-expression of E2F, together with an activated ras oncogene can cause oncogenic transformation of primary rodent fibroblasts [3].

To date four different E2F-like polypeptides have been isolated. E2F-1, 2 and 3 are found only in complex with pRb, whereas E2F-4 interacts preferentially with p107 [3, 15, 19, 22, 24, 30, 36]. How complex formation between E2F and p107 and E2F and p130 is regulated is currently not known. To begin to address the regulation of the E2F/p107 complex and the E2F/p130 complex, we have searched for additional members of the E2F gene family. We report here the cloning of a fifth member of the E2F gene family that interacts preferentially with p130.

Materials and Methods

Yeast Two-hybrid Screen

Yeast strain Y190 [17], containing the 'bait' plasmid pPC97-p107, was transformed with a day 14.5 CD1 mouse embryo library [8] using the lithium acetate method [34]. Two million transformants were selected for growth on plates lacking histidine and supplemented with 25 mM 3-aminotriazole and subsequently analyzed for β-galactosidase activity as previously described [12]. cDNAs library plasmids derived from doubly positive yeast colonies were tested for target specificity by re-transformation with different Gal4-DBD fusion plasmids: pPC97-p107, pPC97-bmi and pPC97 without insert. The partial mouse E2F-5 cDNA was used to screen additional human cDNA libraries. The full length human E2F-5 cDNA described here was isolated from the T84 colon carcinoma library (Stratagene).

Plasmids pPC97-p107 was generated by cloning the pocket region of p107 (amino acids 240–816) in frame with the Gal4 DNA binding domain (amino acids 1–147) of pPC97 [8]. pGST-E2F-5 (A) and (B) were constructed by cloning a fragment of human E2F-5 cDNA encoding amino acids 89–200 (A) or amino acids 89–346 (B) in pGEX-2T. For transfection experiments the following plasmids were used: pSG-Gal4-E2F-1 contains amino acids 284–437 of human E2F-1 [19]. pJ3-Gal4-E2F-4 and pJ3-Gal4-E2F-5 were obtained by cloning a fragment of the human cDNA of E2F-4 (encoding amino acids 276–412) or E2F-5 (encoding amino acids 222–346) in frame with the DNA binding domain of Gal4 in pJ3Ω[33]. pJ3-E2F-5 was constructed by cloning the full length human E2F-5 cDNA (lacking the last 184 nucleotides of 3' non coding sequence) into the mammalian expression vector pJ3Ω. The translation start codon of E2F-5 was preceded by the 10 amino acid epitope (HA) that is recognized by the monoclonal antibody 12CA5. pCMV-DP-1, pCMV-pRb, pCMV-p107, pCMV-p107DE, PCMV-pRbΔ22 have been described previously [20, 41].

Cell Lines

U2-OS and CAMA cells were cultured in Dulbecco's modified Eagle medium (DMEM) supplemented with 10% or 20% fetal calf serum, respectively. Transfections were performed using the calcium phosphate precipitation technique [39].

CAT Assays

U2-OS cells were transiently transfected with the expression vectors as indicated together with 5 μg (Gal4)$_5$-CAT [25] or 2 μg E2F$_4$-CAT [20], 0.2 μg RSV-luciferase and herring sperm carrier DNA to a total amount of 20 μg/10 cm plate. Cells were assayed for CAT and luciferase activity as described previously [2, 3].

Northern Blot Analysis

For E2F-5 expression analysis, total cytoplasmic RNA was prepared from a panel of cell lines. 20 mg of total cellular RNA was electrophoresed through a 1% formaldehyde agarose gel as described [4], transferred to nitrocellulose and probed with a [$^{32}$P]-labeled partial human E2F-5 cDNA (nt. 666–1038). Subsequently, the same filter was probed with a rat α-tubulin cDNA to control for the amount of RNA loaded in each lane.

Immunological Reagents and Immunoprecipitations

To generate antibodies against E2F-5, GST-E2F-5 (A) and (B) (see plasmids) proteins were made in E. coli and purified using gluthatione-sepharose beads. Both proteins were injected in a rabbit in equal amounts. After three rounds of immunization polyclonal serum was obtained. Monoclonal antibodies against E2F-1 (KH20), E2F-4 (RK13), pRb (XZ77) and p107 (SD-4 and 9) have been described previously [3, 20, 21, 41]. The p130 (C20) rabbit polyclonal antiserum was obtained from Santa Cruz Biotechnology Inc. CAMA cells and transfected U2-OS cells were labeled and immunoprecipitated as described previously [3].

Gel Retardation Assays

Gel retardation assays for transiently transfected U-2 OS cells were performed as described previously [20] with minor modifications. 10 μg of whole cell extract was used in a binding buffer containing 20 mM HEPES (pH 7.4), 0.1 M KCl, 1 mM MgCl$_2$, 0.1 mM EDTA, 7% glycerol, 1 mM NaF and 1 μg sonicated salmon sperm DNA in 20 μl reaction volume with 0.5 ng of [$^{32}$P]-labeled oligonucleotide specifying the consensus E2F DNA binding site (Santa Cruz Biotechnology). DNA-protein complexes were allowed to form during an incubation for 20 min. at RT. The reaction products were separated on a 3.5% polyacrylamide gel in 0.25×TBE at 90V at RT for 2.5 hours. The gel was then dried and exposed to film.

Results

Isolation of p107 Binding Proteins

To identify cDNAs encoding polypeptides that interact with p107, a yeast two hybrid screen was performed [14]. Yeast strain Y190 [17], which contains two chromosomally located Gal4-inducible reporter genes: HIS3 and LacZ [12], was co-transformed with the 'bait' plasmid containing the pocket region (amino acids 240–816) of p107 fused to the DNA binding domain (DBD) of Gal4 and a day 14.5 CD1 mouse embryo cDNA library in which each cDNA is individually fused to the transactivation domain of Gal4 [8]. A total of 2 million transformants were placed under selection on plates lacking histidine. Eighty seven surviving colonies were screened for expression of β-galactosidase. cDNA-containing plasmids were rescued from sixteen doubly positive yeast colonies. The specificity of p107-binding was confirmed by re-transformation with plasmids encoding other Gal4-DBD fusions. All sixteen hybrid proteins were found to interact specifically with Gal4-p107. DNA sequence analysis showed that the sixteen cDNA library plasmids rescued from the yeasts were derived from 10 different genes. Three cDNAs were derived from the same gene and showed significant homology to the four known E2Fs. Because of this we named the protein encoded by this cDNA E2F-5.

The partial mouse E2F-5 cDNA was then used to obtain a full length human cDNA clone by screening a human colon carcinoma cDNA library. The longest cDNA (2.1 kb) was sequenced and contained a 1038 bp open reading frame encoding a 346-amino acid protein with a predicted molecular mass of 38 kDa. FIG. 1A shows the E2F-5 cDNA sequence and the deduced amino acid sequence.

Figure 1B:
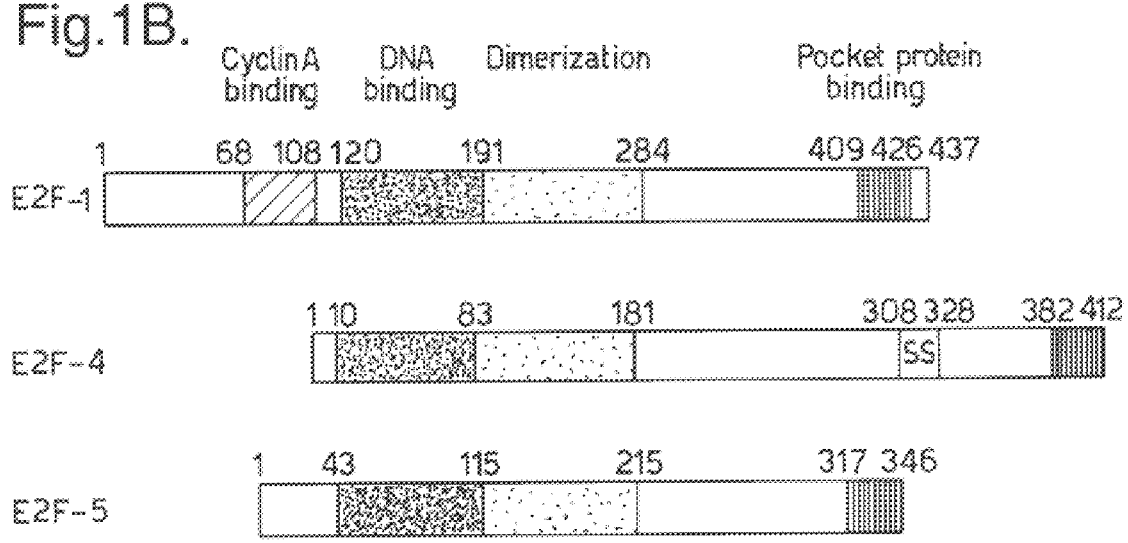
FIG. 1. Human E2F-5 structure (A) Nucleotide sequence and deduced amino acid sequence of the human E2F-5 cDNA. (SEQ ID NOs: 1 and 2, respectively)

E2F-5 is more closely related to E2F-4 (78% similarity) than to E2F-1 (57% similarity). In comparison with E2F-1 and E2F4, three regions of homology can be observed in E2F-5. (FIG. 1B). The DNA binding domain (amino acids 43–115 of E2F-5) shares 93% similarity with the E2F-4 DNA binding region, whereas the juxtaposed DP-1 dimerization domain is 81% similar between E2F-4 and E2F-5. Finally, the carboxyl terminal pocket protein interaction domain of E2F-4 and 5 are 83% similar. E2F-4 and E2F-5 differ from E2F-1 in that both proteins lack the amino terminal motif of E2F-1 that is involved in cyclin A binding. E2F-5 differs from E2F in that it lacks the serine repeat region of E2F-4.

To analyze mRNA expression levels of E2F-5, a human E2F-5 cDNA was used to probe a Northern blot containing total cytoplasmic RNA from a number of human cell lines. The E2F-5 probe detected a low level of a single 2.1 kb transcript in most cell lines. The human CAMA breast carcinoma cell line expressed somewhat higher levels of E2F-5 (FIG. 2).

E2F-5 Contains a Carboxyl-terminal Transactivation Domain

E2F-1 and E2F-4 contain a carboxyl-terminal transactivation domain that overlaps with the pocket protein binding site [3, 18]. To test whether E2F-5 also contains a transactivation domain, we fused the carboxyl terminus of human E2F-5 to the DNA binding domain of Gal4 in the mammalian expression vector pJ3Ω. U2-OS osteosarcoma cells were transiently transfected with a CAT reporter gene harboring five upstream Gal4 sites or cotransfected with the reporter gene and Gal4-E2F expression vectors. FIG. 3 shows that cotransfection of the Gal4 reporter plasmid with the Gal4-E2F-5 expression vectors resulted in a 50-fold activation of the CAT reporter gene. Cotransfection with Gal4-E2F-1 or Gal4-E2F-4 resulted in a two- to three-fold higher activation of the CAT reporter gene (FIG. 3). We conclude that E2F-5 contains a potent carboxyl terminal transactivation domain.

E2F-5 Requires DP-1 for DNA Binding

Both E2F-1 and E2F-4 require dimerization with DP-1 for efficient DNA binding [1, 3, 20, 26]. To investigate whether E2F-5 can bind to a consensus E2F DNA binding site and whether E2F-5 requires DP-1 dimerization in order to bind DNA, we performed a transient transfection experiment. Human U2-OS osteosarcoma cells were transfected with a CAT reporter plasmid in which a core promoter was linked to four upstream E2F sites. FIG. 4 shows that the E2F-CAT reporter plasmid only has low activity when transfected alone in the osteosarcoma cells. Transfection of DP-1 or E2F-5 expression vectors separately did not result in activation of the E2F-CAT reporter (FIG. 4, tracks 2 and 6). Cotransfection of DP-1 and E2F-5 expression vectors resulted in a strong dose-dependent synergistic activation of the CAT reporter (FIG. 4, tracks 3–5). These data indicate that E2F-5 can bind the consensus E2F site and that DNA-binding is DP-1-dependent. Based on these results we conclude that E2F-5 is a genuine member of the E2F gene family.

E2F-5 Transactivation is Suppressed by Pocket Proteins

Transactivation of E2F-1 and E2F-4 is suppressed by pocket protein binding because the transactivation domain of these E2Fs overlaps with the pocket protein interaction surface. To test the effect of pocket protein expression on E2F-5 transactivation we used a transient transfection assay. Since E2F-1 and E2F-4 both require DP-1 dimerization for efficient binding to their respective pocket proteins [3, 20], we measured the effect of pocket protein expression on E2F-5 plus DP-1 activated transcription. U2-OS cells were transfected with the E2F-CAT reporter plasmid together with E2F-5 and DP-1. FIG. 5 (track 3) shows that cotransfection of E2F-5 and DP-1 resulted in a greater than 100-fold activation of the E2F-CAT reporter gene. E2F-5-stimulated transcription was inhibited by cotransfection with pRb, p107 and p130 expression vectors in a dose-dependent fashion. Mutants of pRb (pRbΔ22) and p107 (p107DE) that lack an intact pocket domain were unable to suppress E2F-5 transactivation (FIG. 5, tracks 6 and 9). Significantly, these mutant forms of pRb and p107 also lack growth inhibitory activity [41]. Thus, although this experiment did not allow for an unambiguous identification of the preferred binding partner of E2F-5, it did indicate that E2F-5 transactivation is inhibited by pocket protein binding and that a close correlation exists between the ability of pRb and p107 to cause a growth arrest and their ability to inhibit E2F-5 transactivation. It is important to point out that the U2-OS cells used in this experiment are insensitive to a pRb-or p107-induced growth arrest [41]. The observed effects on E2F-5 transactivation are therefore unlikely to be due to non-specific cell cycle effects of pRb or p107.

E2F-5 Interacts Preferentially with p130 in a Band Shift Assay.

To further investigate the specificity of pocket protein binding by E2F-5, we performed an electrophoresis mobility shift assay (EMSA). U2-OS cells were transiently transfected with DP-1 and E2F-5 expression vectors with or without pRb, p107 or p130 expression vectors. Two days after transfection, whole cell extracts were prepared from transfected cells and incubated with a [$^{32}$P]-labeled oligonucleotide that specifies a consensus E2F site. DNA-protein complexes were separated on a polyacrylamide gel and visualized by radiography. FIG. 6 shows that transfection of E2F-5 and DP-1 expression vectors leads to the appearance of a novel complex that was not observed in the mock-transfected cells (FIG. 6, compare lanes 1 and 2). This complex could be supershifted by cotransfection of p130 expression vector, but not by p107 or pRb expression vectors (FIG. 6, lanes 3–5). These data suggest that of the three pocket proteins tested, p130 has the highest affinity for the E2F-5/DP-1 heterodimer.

E2F-5 Interacts Preferentially with p130 in vivo.

Under physiological conditions, E2F-1 binds preferentially to pRb and E2F-4 to p107 [3, 15, 19, 24]. In transient transfection experiments however, both E2F-1 and E2F-4-activated gene expression can be suppressed by both pRb and p107 [3, 40]. This loss of specificity is probably caused by the transient over-expression of these proteins. To address which of the three members of the retinoblastoma protein family interacts with E2F-5 under physiological conditions, we generated a polyclonal rabbit antiserum against human E2F-5. Initial immunoprecipitation experiments using in vitro transcribed and translated E2F-1, E2F-4 and E2F-5 indicated that the polyclonal E2F-5 serum specifically recognized E2F-5 (data not shown). The E2F-5 antiserum was then used in a sequential immunoprecipitation experiment. CAMA breast carcinoma cells were metabolically labeled with [$^{32}$p]-orthophosphate and non-ionic detergent lysates were prepared. These lysates were subjected to immunoprecipitation with pRb-specific antibody, p107 antibody or p130-specific antiserum. Proteins that were co-immunoprecipitated with pRb, p107 or p130 were released by boiling in SDS-containing buffer, diluted, and re-immunoprecipitated with E2F-5-specific antiserum. FIG. 6 panel B shows that a protein of 47 kDa could be specifically re-immunoprecipitated with E2F-5 antiserum from the p130 immunoprecipitate, but not from pRb or p107 immunoprecipitates. This 47 kDa protein comigrates on SDS polyacrylamide gels with transiently transfected E2F-5 (data not shown). As a control we verified whether pRb and p107 immunoprecipitates contained their respective E2Fs. FIG. 6, panel C shows that pRb did indeed coimmunoprecipitate E2F-1 and p107 brought down E2F-4. Taken together these data indicate that E2F-5 preferentially interacts with p130 in vivo.

Discussion

We report here the isolation of a fifth member of the E2F gene family. E2F-5 has all the hallmarks of a genuine E2F family member: it contains a highly conserved DNA binding domain, a DP-1 dimerization domain and a carboxyl terminal transactivation domain. Furthermore, E2F-5 binds a consensus E2F DNA binding site in a cooperative fashion with DP-1 and can activate the expression of an E2F site-containing reporter gene.

We performed three types of experiments to address with which of the three pocket proteins E2F-5 interacts preferentially in vivo. In transient transfection experiments, E2F-5 transactivation could be suppressed by all three members of the retinoblastoma protein family, pRb, p107 and p130. In this respect E2F-5 resembles E2F-1 and E2F4, since both E2F-1 and E2F-4 transactivation can be inhibited in transient transfection assays by pRb as well as p107 [3, 40]. This apparent lack of specificity in a transient transfection assay is probably the result of the high transient expression levels of both the E2F and the pocket proteins in the transiently transfected cells. The relatively low level of inhibition of E2F-5 transactivation by p130 in the transient transfection experiment (FIG. 5) is the result of the low level of p130 expression since in transiently transfected cells, p107 was found to be expressed at a 10-fold higher level as compared to p130 (data not shown). Two additional experiments were performed to address pocket protein specificity of E2F-5. In the first experiment, cells were transiently transfected with E2F-5 and DP-1 expression vectors in the presence or absence of expression vectors for all three pocket proteins. Subsequently, band shift assays were performed using extracts from the transfected cells with an oligonucleotide specifying a consensus E2F binding site. Only cotransfection of p130 could cause a supershift of the E2F-5/DP-1 complex (FIG. 6). In the band shift experiment, only complexes between pocket proteins and E2F-5 that are stable for prolonged periods of time are detected as E2F/pocket protein "supershifted" complexes. Thus, even though p130 was expressed at a lower level than p107, the complex between E2F-5 and p130 was more stable than the p107/E2F-5 complex (FIG. 6). In a similar experiment, we were able to "supershift" an E2F-4 DNA binding complex with p107, but not with pRb (R.L.B and R.B, unpublished data). This result suggests that mobility shift experiments can be potentially useful to address pocket protein specificity of E2Fs. Consistent with the results of the mobility shift assay, we found that in non-transfected metabolically labeled CAMA breast carcinoma cells, E2F-5 could be co-immunoprecipitated with p130, and not with p107 or pRb (FIG. 7). Taken together, our data indicate that under physiological conditions, E2F-5 preferentially associates with p130.

The finding that E2F-5 interacted with p130 but not with p107 was somewhat unexpected because p130 and p107 are structurally closely related and indeed p107 and p130 share the ability to bind cyclins A and E [16, 32, 41]. On the other hand, p107 and p130 differ in their ability to interact with D type cyclins in vivo as only p107, and not p130, co-immunoprecipitates with anti D type cyclin antibodies [32]. Importantly, the appearance of the p130/E2F and p107/E2F complexes differs in the cell cycle [9, 10, 29, 35, 37]. This suggests that p107 and p130 have distinct functions during the cell cycle. The preferential binding of E2F-5 by p130 is consistent with such a distinct role for p130 in cell cycle regulation.

Our finding that E2F-5 can bind to a consensus E2F site by no means rules out the possibility that E2F-5 interacts with a discrete subset of E2F sites in vivo that is distinct from the E2F sites that are bound by the other members of the E2F gene family. Consistent with such a binding site preference of the different E2Fs is the finding that the E2F sites that are present in the thymidine kinase gene promoter and in the b-myb promoter interact preferentially with E2F/p107 complexes [28, 31]. Since complexes between E2F and p130 are found mostly in quiescent cells and disappear quickly after cells emerge from quiescence, it is likely that E2F-5-responsive genes are involved in the early responses of resting cells to growth factor stimulation [10]. The availability of the p130-interacting E2F-5, should allow us to identify E2F-5-responsive genes.

Acknowledgments

We thank P. Chevray for the gift of the mouse embryo cDNA library and yeast expression vectors, S. Elledge for yeast strain Y1090, M. Alkema for the Gal4-bmi yeast expression vector, G. Hannon for the gift of the p130 expression vector, A. Bes-Gennissen for the gift of human cell line RNA and Y. Ramos for preparing the Northern blot. This work was supported by a grant from the Netherlands Organization for Scientific Research (NWO).

REFERENCES FOR EXAMPLE 1

1. Bandara, L. R., V. M. Buck, M. Zamanian, L. H. Johnston and N. B. La Thangue. 1993. Functional synergy between DP-1 and E2F-1 in the cell cycle-regulating transcription factor DRTF1/E2F. Embo J. 12:4317–4324.
2. Beijersbergen, R. L., E. M. Hijmans, L. Zhu and R. Bernards. 1994. Interaction of c-Myc with the pRb-related protein p107 results in inhibition of c-Myc-mediated transactivation. Embo J. 13:4080–4086.
3. Beijersbergen, R. L., R. Kerkhoven, L. Zhu, L. Carlee, P. M. Voorhoeve and R.
Bernards. 1994. E2F-4, a new member of the E2F gene family, has oncogenic activity and associates with p107 in vivo. Genes, Dev. 8:2680–2690.
4. Bernards, R., S. K. Dessain and R. A. Weinberg. 1986. N-myc amplification causes down-modulation of MHC class I antigen expression in neuroblastoma. Cell. 47:667–674.
5. Buchkovich, K., L. A. Duffy and E. Harlow. 1989. The retinoblastoma protein is phosphorylated during specific phases of the cell cycle. Cell. 58:1097–1105.
6. Chellappan, S. P., S. Hiebert, M. Mudryj, J. M. Horowitz and J. R. Nevins. 1991. The E2F transcription factor is a cellular target for the RB protein. Cell. 65:1053–1061.
7. Chen, P. L., P. Scully, J. Y. Shew, J. Y. Wang and W. H. Lee. 1989. Phosphorylation of the retinoblastoma gene product is modulated during the cell cycle and cellular differentiation. Cell. 58:1193–1198.
8. Chevray, P. M. and D. Natans. 1992. Protein interaction cloning in yeast: identification of mammalian proteins that react with the leucine zipper of jun. Proc. Natl. Acad. Sci. USA. 89:5789–5793.
9. Chittenden, T., D. M. Livingston and J. A. DeCaprio. 1993. Cell cycle analysis of E2F in primary human T cells reveals novel E2F complexes and biochemically distinct forms of free E2F. Mol Cell Biol. 13:3975–3983.
10. Cobrinik, D., P. Whyte, D. S. Peeper, T. Jacks and R. A. Weinberg. 1993. Cell cycle-specific association of E2F with the p130 E1A-binding protein. Genes, Dev. 7:2392–2404.
11. DeCaprio, J. A., J. W. Ludlow, D. Lynch, Y. Furukawa, J. Griffin, H. Piwnica-Worms, C.-M. Huang and D. M. Livingston. 1989. The product of the retinoblastoma gene has properties of a cell cycle regulatory element. Cell. 58:1085–1095.
12. Durphee, T., K. Becherer, P.-L. Chen, S.-H. Yeh, Y. Yang, A. E. Kilburn, W.-H. Lee and E. S. J. 1993. The retinoblastoma protein associates with the protein phosphatase type 1 catalytic subunit. Genes, Dev. 7:555–569.
13. Farnham, P. J., J. E. Slansky and R. Kollmar. 1993. The role of E2F in the mammalian cell cycle. Biochim Biophys Acta. 1155:125–131.
14. Fields, S. and O. Song. 1989. A novel genetic system to detect protein-protein interactions. Nature. 340:245–246.
15. Ginsberg, D., G. Vairo, T. Chittenden, X. Zhi-Xiong, G. Xu, W. K. L., J. A. DeCaprio, L. J. B. and D. M. Livingston. 1994. E2F-4, a new member of the E2F transcription factor family, interacts with p107. Genes, Dev. 8:2665–2679.
16. Hannon, G. J., D. Demetrick and D. Beach. 1993. Isolation of the Rb-related p130 through its interaction with CDK2 and cyclins. Genes, Dev. 7:2378–2391.
17. Harper, J. W., G. R. Adami, N. Wei, K. Keyomarsi and S. J. Elledge. 1993. The p21 Cdk-interacting protein Cip1 is a potent inhibitor of G1 cyclin-dependent kinases. Cell. 75:805–816.
18. Helin, K., E. Harlow and A. Fattaey. 1993. Inhibition of E2F-1 transactivation by direct binding of the retinoblastoma protein. Mol Cell Biol. 13:6501–6508.
19. Helin, K., J. A. Lees, M. Vidal, N. Dyson, E. Harlow and A. Fattey. 1992. A cDNA encoding a pRB-binding protein with properties of the transcription factor E2F. Cell. 70:337–350.
20. Helin, K., C.-L. Wu, A. R. Fattaey, J. A. Lees, B. D. Dynlacht, C. Ngwu and E. Harlow. 1993. Heterodimerization of the transcription factor E2F-1 and DP-1 leads to cooperative trans-activation. Genes, Dev. 7:1850–1861.
21. Hu, Q., C. Bautista, G. Edwards, D. Defeo-Jones, R. Jones and E. Harlow. 1991. Antibodies specific for the human retinoblastoma protein identify a family of related polypeptides. Mol. Cell. Biol. 11:5792–5799.
22. Ivey-Hoyle, M., R. Conroy, H. E. Huber, P. J. Goodhart, A. Oliff and D. C. Heimbrook. 1993. Cloning and characterization of E2F-2, a novel protein with the biochemical properties of transcription factor E2F. Mol Cell Biol. 13:7802–7812.
23. Johnson, D. G., J. K. Schwarz, W. D. Cress and J. R. Nevins. 1993. Expression of transcription factor E2F-1 induces quiescent cells to enter S phase. Nature. 365:349–352.
24. Kaelin, W. G., W. Krek, W. R. Sellers, J. A. DeCaprio, F. Ajchenbaum, C. S. Fuchs, T. Chittenden, Y. Li. P. Farnham, M. A. Blanar, D. M. Livingston and E. K. Flemington. 1992. Expression cloning of a cDNA encoding a retinoblastoma-binding protein with E2F-like properties. Cell. 70:351–364.
25. Kato, G. J., J. Barrett, G. M. Villa and C. V. Dang. 1990. An amino-terminal c-myc domain required for neoplastic transformation activates transcription. Mol. Cell. Biol. 10:5914–5920.
26. Krek, W., D. M. Livingston and S. Shirodkar. 1993. Binding to DNA and the retinoblastoma gene product promoted by complex formation of different E2F family members. Science. 262:1557–1560.
27. La Thangue, N. B. 1994. DP and E2F proteins: components of a heterodimeric transcription factor implicated in cell cycle control. Curr. Opin. Cell Biol. 6:443–450.
28. Lam, E. W. and R. J. Watson. 1993. An E2F-binding site mediates cell-cycle regulated repression of mouse B-myb transcription. Embo J. 12:2705–2713.
29. Lees, E., B. Faha, V. Dulic, S. I. Reed and E. Harlow. 1992. Cyclin E/cdk2 and cyclin A/cdk2 kinases associate with p107 and E2F in a temporally distinct manner. Genes Dev. 6:1874–1885.
30. Lees, J. A., M. Saito, M. Vidal, M. Valentine, T. Look, E. Harlow, N. Dyson and K. Helin. 1993. The retinoblastoma protein binds to a family of E2F transcription factors. Mol Cell Biol. 13:7813–7825.
31. Li, L. J., G. S. Naeve and A. S. Lee. 1993. Temporal regulation of cyclin A-p107 and p33cdk2 complexes binding to a human thymidine kinase promoter element important for G1-S phase transcriptional regulation. Proc Natl Acad Sci U S A. 90:3554–3558.
32. Li, Y., C. Graham, S. Lacy, A. M. V. Duncan and P. Whyte. 1993. The adenovirus E1A-associated 130-kD protein is encoded by a member of the retinoblastoma gene family and physically interacts with cyclins A and E. Genes, Dev. 7:2366–2377.
33. Morgenstern, J. and H. Land. 1990. A series of mammalian expression vectors and characterisation of their expression of a reporter gene in stably and transiently transfected cells. Nucleic Acid Res. 18:1068.
34. Schiestl, R. H. and R. D. Gietz. 1989. High efficiency transformation of intact yeast cells using single stranded nucleic acid as a carrier. Curr. Genet. 16:339–346.
35. Schwarz, J. K., S. H. Devoto, E. J. Smith, S. P. Chellappan, L. Jakoi and J. R. Nevins. 1993. Interactions of the p107 and Rb proteins with E2F during the cell proliferation response. Embo J. 12:1013–1020.
36. Shan, B., X. Zhu, P. L. Chen, T. Durfee, Y. Yang, D. Sharp and W. H. Lee. 1992. Molecular cloning of cellular genes encoding retinoblastoma-associated proteins: identification of a gene with properties of the transcription factor E2F. Mol Cell Biol. 12:5620–5631.
37. Shirodkar, S., M. Ewen, J. A. DeCaprio, J. Morgan, D. M. Livingston and T. Chittenden. 1992. The transcription factor E2F interacts with the retinoblastoma product and a p107-cyclin A complex in a cell cycle-regulated manner. Cell. 68:157–166.
38. Slansky, J. E., Y. Li, W. G. Kaelin and P. J. Farnham. 1993. A protein synthesis-dependent increase in E2F-1 mRNA correlates with growth regulation of the dihydrofolate reductase promoter. Mol Cell Biol. 13:1610–1618.
39. Van der Eb, A. J. and F. L. Graham. 1980. Assay of transforming activity of tumor virus DNA. Meth. Enzymol. 65:826–839.
40. Zamanian, M. and N. B. La Thangue. 1993. Transcriptional repression by the Rb-related protein p107. Mol Biol of Cell. 4:389–396.
41. Zhu, L., S. van den Heuvel, K. Helin, A. Fattaey, M. Ewen, D. Livingston; N. Dyson and E. Harlow. 1993. Inhibition of cell proliferation by p107, a relative of the retinoblastoma protein. Genes Dev. 7:1111–1125.

EXAMPLE 2

Summary

The transcription factor DRTF1/E2F is implicated in the control of cellular proliferation due to its interaction with key regulators of cell cycle progression, such as the retinoblastoma tumour suppressor gene product and related pocket proteins, cyclins and cyclin-dependent kinases. DRTF1/E2F DNA binding activity arises when a member of two distinct families of proteins, DP and E2F, interact as DP/E2F heterodimers. Here, we report the isolation and characterisation of a new member of the E2F family of proteins, called E2F-5. E2F-5 was isolated through a yeast two hybrid assay in which a 14.5 d.p.c. mouse embryo library was screened for molecules capable of binding to murine DP-1, but also interacts with all known members of the DP family of proteins. E2F-5 exists as a physiological heterodimer with DP-1 in the generic DRTF1/E2F DNA binding activity present in mammalian cell extracts, an interaction which results in co-operative DNA binding activity and transcriptional activation through the E2F site. A potent transcriptional activation domain, which functions in both yeast and mammalian cells and resides in the C-terminal region of E2F-5, and expression of the pRb-related protein p107, rather than pRb, inactivates the transcriptional activity of E2F-5. Comparison of the sequence of E2F-5 with other members of the family indicates that E2F-5 shows a greater level of similarity with E2F-4 than to E2F-1, -2 and -3. The structural and functional similarity of E2F-5 and E2F-4 defines a subfamily of E2F proteins.

Introduction

Considerable evidence suggests that the cellular transcription factor DRTF1/E2F is involved in co-ordinating transcription with cell cycle progression. For example, DRTF1/E2F appears to be one of the principal targets through which the retinoblastoma tumour suppressor gene product (pRb) exerts its negative effects on cellular proliferation (La Thangue, 1994). Thus, by regulating the transcriptional activity of DRTF1/E2F and hence the activity of target genes, many of which encode proteins required for cell cycle progression (Nevins, 1992), pRb is able to influence progression through the early cell cycle. Natural mutations in Rb, which occur in human tumour cells, encode proteins which fail to bind to DRTF1/E2F (Bandara et al., 1992; Heibert et al., 1992; Zamanian and La Thangue. 1992), underscoring the correlation between de-regulating DRTF1/E2F and aberrant cell growth. Furthermore, the transforming activity of viral oncoproteins, such as adenovirus E1a. human papilloma virus E7 and SV40 large T antigen, correlates with their ability to de-regulate DRTF1/E2F through the sequestration of pRb and related proteins (Nevins, 1992), providing further support for this view.

Other molecules which play a central role in the cell cycle also interact with DRTF1/E2F. Cyclins A and E, together with the catalytic subunit cdk2, bind to DRTF1/E2F either directly by contacting the DNA binding components in the transcription factor (Krek et al., 1994) or indirectly through contacts which occur in the spacer region of the pRb-related pocket proteins p107 or p130 (Lees et al., 1992; Cobrinik et al., 1993). Although the role of the cyclin-cdk complex which associates with p107 and p130 has yet to be resolved, the direct interaction between the cyclin A/cdk2 kinase complex and DRTF1/E2F has been shown to affect its DNA binding activity (Krek et al., 1994).

The molecular composition of DRTF1/E2F is beginning to be uncovered. It is now clear that the generic DNA binding activity DRTF1/E2F arises when members of two distinct families of proteins interact as DP/E2F heterodimers (La Thangue, 1994), the prototype molecules of each family being DP-1 (Girling et al., 1993) and E2F-1 (Helin et al., 1992; Kaelin et al., 1992; Shan et al., 1992). A small region of similarity between both proteins allows them to interact as a heterodimer (Bandara et al., 1993; Helin et al., 1993; Krek et al., 1993), this region being conserved in all DP and E2F family members isolated to date (Girling et al., 1994), thus allowing diverse combinatorial interactions to occur.

During cell cycle progression the association of pRb, p107 and p130 occurs in a temporally-regulated manner, each protein having its own characteristic profile of interactions with DRTF1/E2F (Shirodkar et al., 1992; Schwarz et al., 1993; Cobrinik et al., 1993). From the E2F family members isolated to date, E2F-1, –2, and -3 recognise pRb (Ivey-Hoyle et al., 1993; Lees et al., 1993) and E2F-4 the p107 protein (Beijersbergen et al., 1994; Ginsberg et al., 1994), a likely explanation being that the temporal interactions of pocket proteins reflect the regulated composition and/or availability of the E2F family member in the E2F/DP heterodimer.

Although in many types of cells DP-1 is a frequent DNA binding component of DRTF1/E2F, being present in the varying forms which occur during cell cycle progression (Bandara et al., 1994), other DP family members, such as DP-2, are expressed in a tissue-restricted fashion (Girling et al., 1994). It would appear likely therefore that the molecular composition of DRTF1/E2F is influenced by cell cycle progression and the phenotype of the cell.

The complexity of the E2F family of proteins has yet to be elucidated. In order to address this question we have performed a yeast-based two hybrid screen to define new members of the family. Here, we report the isolation and characterization of murine E2F-5, a new member of the E2F family. E2F-5 interacts with all the known members of the DP family of proteins. In mammalian cell extracts E2F-5 exists as a physiological heterodimer with DP-1, an interaction which results in co-operative DNA binding and transcriptional activation through the E2F site. E2F-5 possesses a potent trans-activation domain which is specifically inactivated upon pocket-protein binding. The protein sequence and molecular organisation of E2F-5 is more closely related to E2F-4 than other members of the family, defining for the first time a subfamily of E2F proteins which are functionally and structurally related.

Results

Isolation of E2F-5

Figure 8:
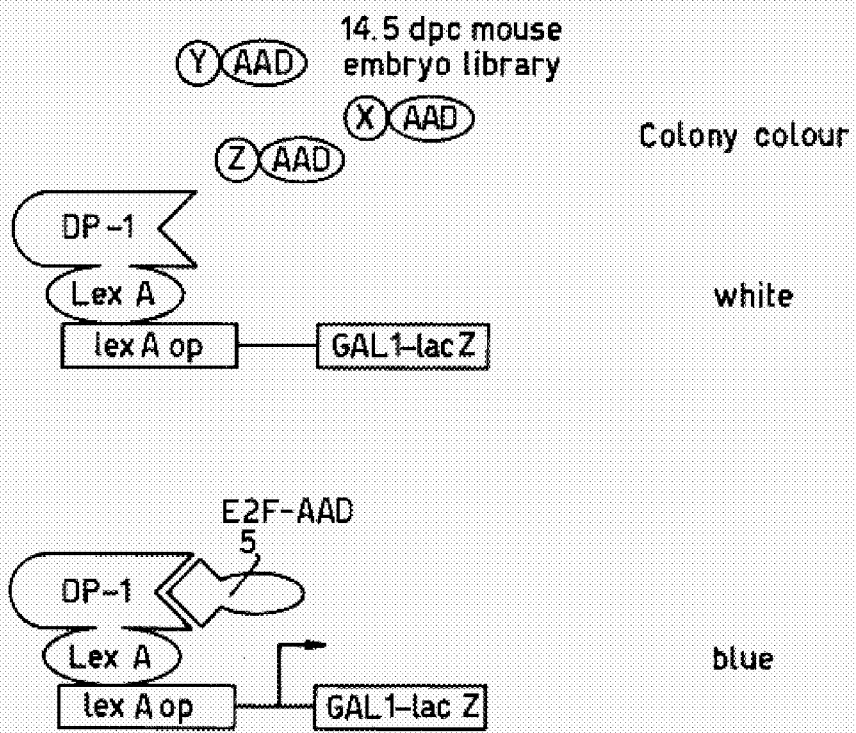

In order to explore the diversity of the E2F family of proteins we employed a yeast two hybrid-based strategy (Fields and Song, 1989) to identify new members (FIG. 8). We chose to use DP-1 as the bait, since DP-1 is a physiological and frequent partner for E2F-family members (Bandara et al., 1993; Bandara et al., 1994). An activation domain tagged cDNA library prepared from a 14.5 d.p.c. mouse embryo (Chevray and Nathans, 1992) was screened for hybrid proteins capable of interacting with LexA-DP-1. One of the clones identified encoded a hybrid protein which by several criteria specifically interacted with LexA-DP-1. Partial analysis of the cDNA sequence indicated extensive similarity to E2F family members, and thus a cDNA clone encoding the complete protein sequence was further isolated from an F9 EC cDNA library. Comparison of the protein sequence with other members of the E2F family indicated that the cDNA clone encoded a novel member. Following the designation adopted for previously isolated E2F proteins as E2F-1, -2, -3 and -4, we refer to this clone as E2F-5.

The predicted size of murine E2F-5 is 335 residues (FIG. 9a). This prediction is based on the position of the first potential initiating methionine, together with the extensive homology existing to the human E2F-5 sequence in which translation initiates at the same methionine (Hijmans et al., submitted). E2F-5 contains extensive sequence similarity with the domains conserved between other E2F family members (Ivey-Hoyle et al., 1993; Lees et al., 1993; Beijersbegen et al., 1994; Ginsberg et al., 1994). For example, the DNA binding domain shows 48% identity with E2F-1 and 87% with E2F-4 (FIG. 9b and c). Within this area, a C-terminal sub-domain contains the only region of similarity with members of the DP family (indicated in FIGS. 9b and c). This region, which is known as the DEF box (Girling et al., 1994; Lam and La Thangue, 1994), is intimately involved in the formation of the DP/E2F heterodimer (Bandara et al., 1993; Bandara and La Thangue, in preparation). The residues conserved within the DEF box between DP and E2F proteins are also perfectly conserved within E2F-5 (FIG. 9c), underscoring the potential importance of this sub-domain in formation of the DP/E2F heterodimer.

Several additional regions are conserved between E2F-5 and the other family members. The marked box (Lees et al., 1993) and pocket-protein binding domain show 58% and 50% identity to these regions in E2F-1 and 75% and 72% to the same regions in E2F-4 (FIG. 9b and 9c). The positions of the hydrophobic residues in the leucine zip region are also conserved with other E2F family members (FIG. 9c). Indeed. E2F-5 may form a longer zip than E2F-1, -2 and -3 because hydrophobic residues in E2F-5 are in register with the heptad repeat at two further C-terminal positions (L144 and V151; see FIG. 9c).

The features of E2F-5 suggest a closer relationship with E2F-4 rather than with E2F-1, -2 and -3. Its organisation resembles that of E2F-4 in that the protein does not extend much further then the N-terminus of the DNA binding domain, and both proteins lack the N-terminal cyclin A binding domain which occurs in the other E2Fs (FIG. 9b). Furthermore, the protein sequence comparison indicates that E2F-5 and -4 are more related to each other than either is to the remaining members of the family. This is particularly evident across the conserved domains, where many residues are common between E2F-5 and -4 but not between E2F-1, -2 and -3 (FIG. 9c). Overall, E2F-5 contains 70% amino acid residues identical with E2F-4 and 38% with E2F-1. Thus, based on this similarity, E2F-5 and -4 represent one sub-family of the E2F family of proteins whilst E2F-1, -2 and -3, because of their close similarity, represent another.

Binding and Transcriptional Co-operation with DP Family Members

Generic DRTF1/E2F DNA binding activity arises when a DP family member interacts with an E2F family member (La Thangue, 1994). For DP-1 and E2F-1, the interaction results in co-operative transcriptional activation, DNA binding and interaction with pRb (Bandara et al., 1993 Helin et al., 1993; Krek et al., 1993). We were therefore interested to determine whether E2F-5 could co-operate with DP family members.

To answer these questions, we first used the yeast two hybrid assay with different DP molecules represented in the hybrid bait as LexA fusion proteins (FIG. 8). Either E2F-5 or E2F-1 were expressed as activation domain (GAD) tagged hybrid proteins and the degree of transcriptional activation of a LexA reporter construct assessed by measuring β-galactosidase activity. Both E2F-5 and E2F-1 were equally capable of interacting with all known members of the DP family of proteins, that is DP-1, -2, -3 and Drosophila DP (data not shown).

We next assessed if E2F-5 could co-operate with DP-1 to activate transcription through the E2F binding site. For this we used a yeast assay in which E2F-5 and DP-1 were expressed together or alone and the transcriptional activity of an E2F site reporter construct, p4xWT CYC1, measured (FIG. 10a). In previous studies, this assay has been used to measure the co-operation between E2F-1 and DP-1 (Bandara et al., 1993). The transcriptional activity of the reporter was not significantly affected following the expression of the DP-1 hybrid proteins and only marginally by the E2F-5 hybrid (FIG. 10b). However, when both were expressed together, reporter activity was stimulated greater than 6-fold (FIG. 10b). The activity of p4xMT CYC1, a derivative of p4xWT CYC1 which carries mutant E2F binding sites (FIG. 10a; Bandara et al., 1993), was unaffected in the same conditions (data not shown). We conclude therefore that E2F-5 co-operates with DP-1.

Transcriptional Activation and Pocket Protein Regulation of E2F-5

The ability of E2F-5 to activate transcription was assessed in both yeast and mammalian cells. To assay transcriptional activity in yeast, a C-terminal region (from residue 198 to 335) of E2F-5 was fused to LexA, and the activity of a reporter construct driven by LexA binding sites assessed (FIG. 11a). The E2F-5 protein contains a potent trans activation domain since the activity of the reporter in the presence of pLEX.E2F-5 was much greater than when the vector alone was expressed (FIG. 11b); similarly, LexA E2F-1 was capable of activating transcription (FIG. 11b). Thus, E2F-5 activates transcription efficiently in yeast.

To confirm these results in mammalian cells and assess the functional consequences of the interaction of pocket-proteins with E2F-5, we fused the same region of E2F-5 to the Gal4 DNA binding domain and used transient transfection assays to study the transcriptional activity of a reporter construct driven by Gal4 binding sites, pGAL-CAT (FIG. 12a). In 3T3 cells, E2F-5 activated transcription efficiently relative to the activity of the Gal4 DNA binding domain alone (FIG. 12b) since the transcriptional activity of pGAL-CAT was 15-fold greater in the presence of pGAL-E2F-5 relative to pG4. Similar results were obtained in a variety of other cell types (data not shown), indicating that E2F-5 contains a trans-activation domain which functions in mammalian cells.

We then used the transcriptional activity of E2F-5 to assess the functional consequences of an interaction with either pRb or p107. As controls for wild-type pRb and p107, we studied the activity of RbA22, a protein encoded by a naturally-occurring mutant allele of Rb which fails to interact with DRTF1/E2F (Zamanian and La Thangue, 1992) and the activity of anti-sense p107 RNA (Zamanian and La Thangue, 1993). Neither wild-type pRb or RbΔ22 significantly affected the activity of E2F-5, since in the presence of either pCMVHRb or pCMVHRbΔ22 the activity of pGAL-CAT was not affected (FIG. 12b). In contrast, co-expressing p107 (from pCMV107) with E2F-5 reduced the transcriptional activity of E2F-5, an effect which was specific since anti-sense p107 (from pCMV107AS) had no effect (FIG. 12b). We conclude that p107 inactivates the transcriptional activity of E2F-5 in mammalian cells. Using a similar experimental strategy, the p130 protein was shown to inactivate the transcriptional activity of E2F-5 (data not shown).

E2F-5 is a Physiological DNA Binding Component of DRTF1/E2F

In order to determine if E2F-5 is a physiological DNA binding component of the generic DRTF1/E2F DNA binding activity defined in extracts prepared from mammalian cells, two different anti-E2F-5 peptide sera were prepared against distinct peptide sequences; both antisera specifically reacted with a GST-E2F-5 fusion protein (data not shown).

Figure 13:
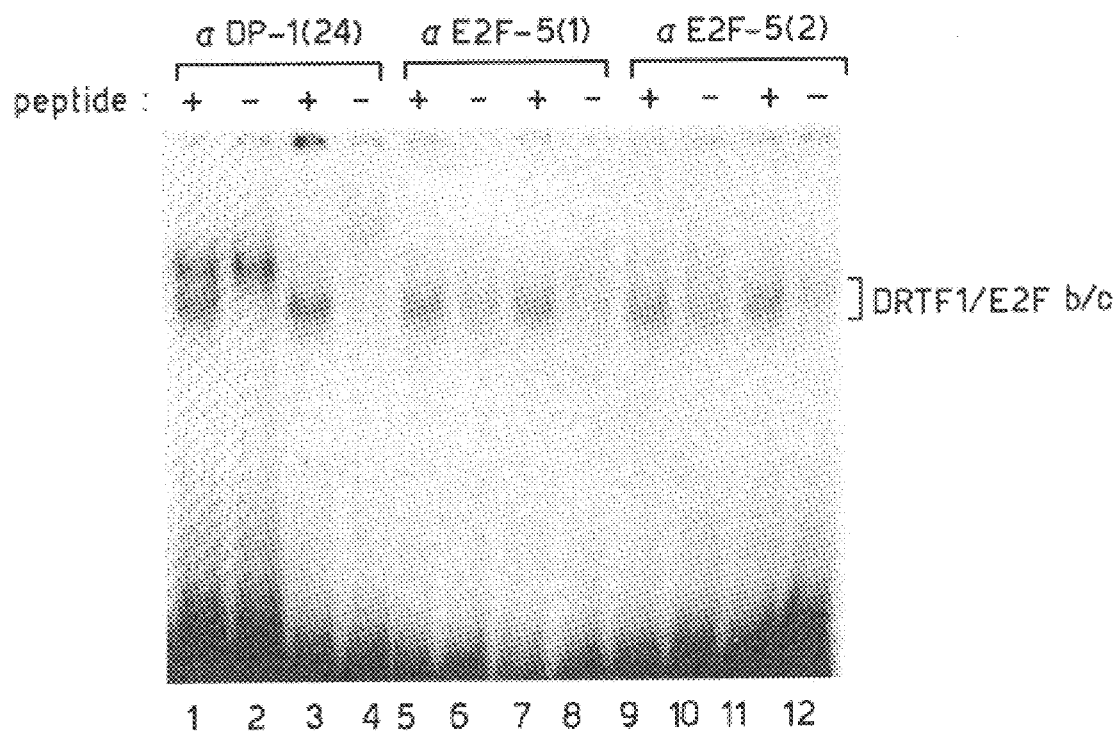

The effect of these antisera on DRTF1/E2F DNA binding activity was studied by gel retardation assays performed with extracts from murine F9 embryonal carcinoma (F9 EC) cells. Previous studies have shown that DP-1 is a frequent, possibly universal, component of the DRTF1/E2F DNA binding activity in F9 EC cell extracts (Girling et al., 1993; Bandara et al., 1993), an example of which is shown in FIG. 13 (tracks 1 to 4). Both anti-E2F-5 sera disrupted DRTF1/E2F DNA binding activity, an effect which was specific since it was not apparent in the presence of the homologous peptide (FIG. 13, tracks 5 through to 12). Although anti-E2F-5 caused a significant decrease in DNA binding activity, the effect was clearly less marked than that caused by anti-DP-1 (FIG. 13, compare tracks 1 through 4 to 5 through 12). This may be because E2F-5 is present in a sub-population of DP-1/E2F heterodimers in F9 EC cell extracts, a situation contrasting with that observed for DP-1.

DNA Binding Properties of E2F-5

Figure 14:
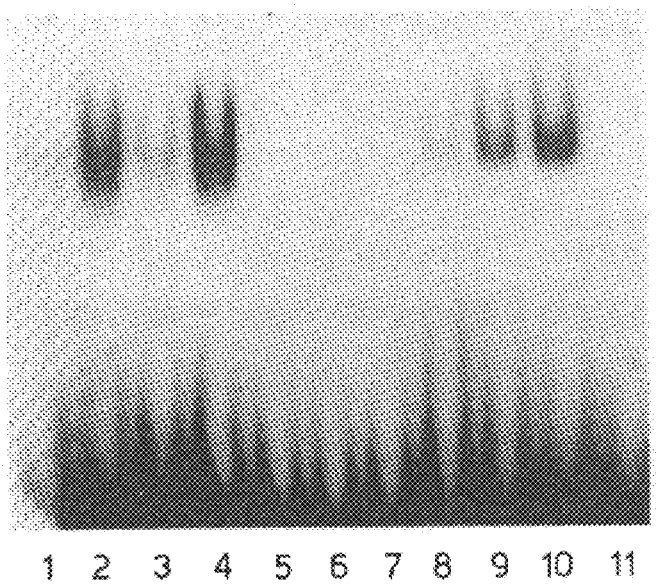

To study the DNA binding properties of E2F-5 we expressed and purified E2F-5 as a GST fusion protein. Consistent with previous results (Bandara et al., 1993), GST-DP-1 co-operated with GST-E2F-1 in binding to the E2F site, although E2F-1 possessed significant DNA binding activity when assayed alone (FIG. 14, compare tracks 1 through 4). In contrast, E2F-5 alone possessed barely detectable DNA binding activity (FIG. 14, tracks 5 through 7). However, the co-operation between E2F-5 and DP-1 was considerably greater than between E2F-1 and DP-1 (FIG. 13, tracks 8 through 10). Thus, E2F-5 and DP-1 co-operate in DNA binding activity.

Levels of E2F-5 RNA

Figure 15:
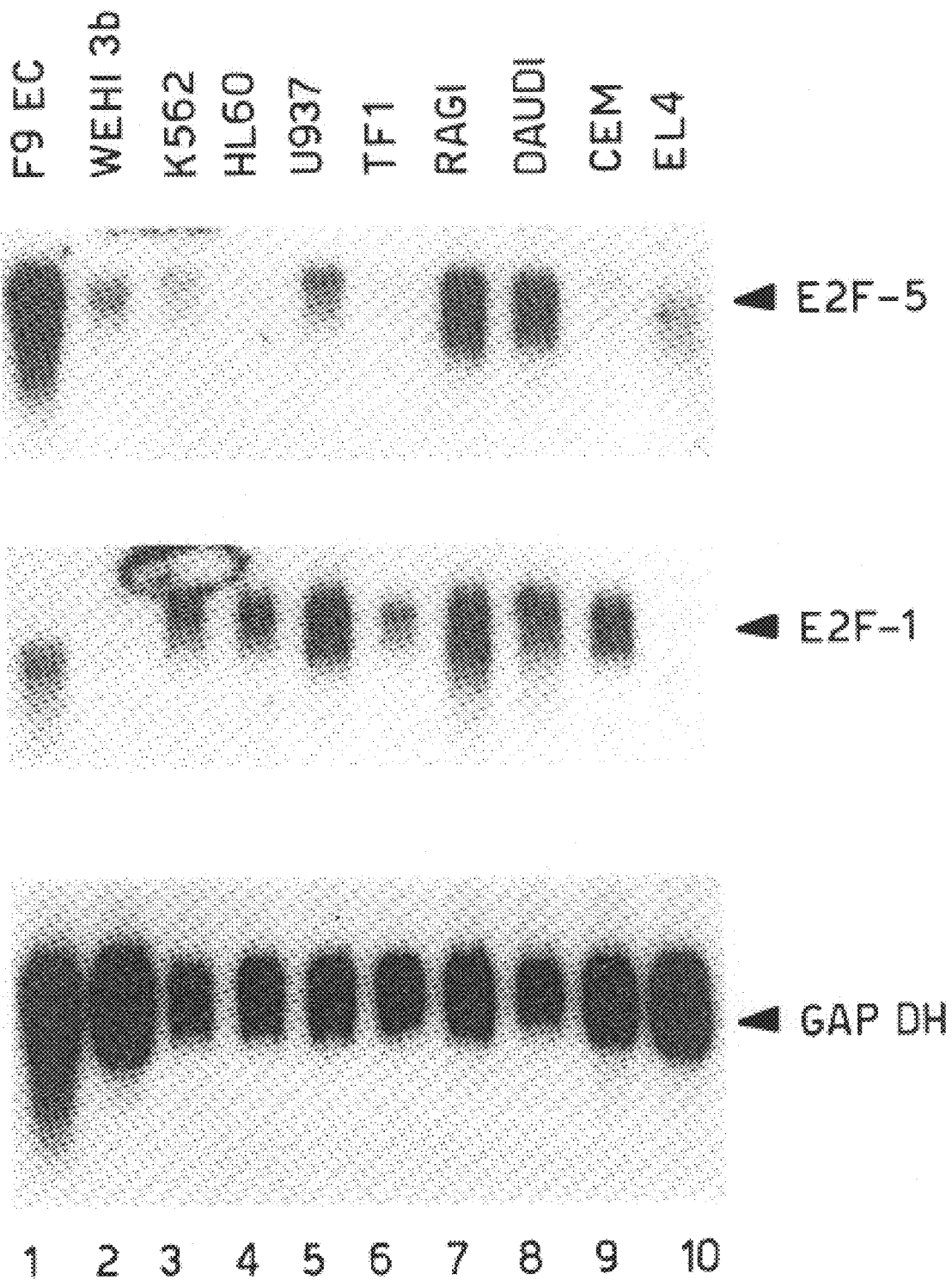

We were interested to determine the levels of E2F-5 RNA in different cell lines and, moreover, compare E2F-5 levels to other members of the E2F family. For this, RNA was prepared from asynchronous cultures of F9 EC cells together with a variety of leukaemic cell lines, and the level of E2F-5 RNA assessed by Northern blotting. The amount of E2F-5 RNA varied considerably from cell line to cell line; F9 EC cells and some of the leukaemic cell lines, for example, DAUDI and RAGI expressed high levels (FIG. 15, tracks 1, 7 and 8). In contrast, HL60 and TF1 contained low levels of E2F-5 RNA (FIG. 15, tracks 4 and 6). This profile of E2F-5 RNA levels differed considerably from the levels of E2F-1. For example, significant levels of E2F-1 RNA were present in K562, HL60 and TF-1 cells in contrast to E2F-5 (FIG. 15, tracks 3,4 and 6). The converse situation was apparent in EL4 cells where E2F-5 levels were high and E2F-1 low (FIG. 15, track 10). We conclude that E2F-5 RNA levels are influenced by the cell type, and that there is little correlation between the levels of E2F-5 and E2F-1 RNA.

Discussion

E2F-5 and E2F-4 are a Sub-family of E2F Proteins

We report the isolation and characterisation of the fifth member of the E2F family of proteins, E2F-5. Although many of the domains in E2F-5, such as the potential leucine zip, the marked box and the pocket protein binding region, are conserved with other members of the E2F family, the lack of N-terminal sequence outside of the DNA binding domain indicates a structural organisation similar to E2F-4 (Beijersbergen et al., 1994; Ginsberg et al., 1994). The other members of the E2F family, E2F-1, -2, and -3, have extended N-termini within which a domain capable of interacting with cyclin A resides (Krek et al., 1994). It has been suggested that the role of this domain is to recruit a cyclin A/cdk2 kinase to the DP-1/E2F heterodimer which results in the subsequent phosphorylation of DP-1, the functional consequence being reduced DNA binding activity of the DP-1/E2F heterodimer (Krek et al., 1994). Such a mechanism may be important in regulating the transcriptional activity of E2F site-dependent genes at later times during cell cycle progression. The absence of a cyclin A binding domain in E2F-5 (and E2F-4) suggests that the DNA binding activity of the E2F-5/DP-1 heterodimer may be down-regulated through other mechanisms. Indeed, a possible scenario through which this could be achieved would be through the p107 and/or p130 proteins since the spacer region in these proteins can bind either cyclin A/cdk2 or cyclin E/cdk2 complexes (Lees et al., 1993; Cobrinik et al., 1993; Hannon et al., 1993; Li et al., 1993). It is possible that these pocket proteins replace the role of cyclin A-binding E2F family members and recruit cyclin/cdk complexes to the DP/E2F heterodimer.

Comparison of the protein sequence of E2F-5 with other members of the E2F family indicated a closer relationship with E2F-4 than with E2F-1, -2, and -3. Interestingly, E2F-4 is the only known member of the family which is capable of interacting with p107 in physiological conditions (Beijersbergen et al., 1994; Ginsberg et al., 1994). We have shown that the transcriptional activity of E2F-5 can be inactivated by p107 or p130 rather than by pRb. However, this may reflect the closer relationship of p107 to p130 than with pRb (Ewen et al., 1991; Cobrinik et al., 1993; Li et al., 1993) and may not therefore entirely reflect physiological interactions. Consistant with this idea is the result that human E2F-5 has been shown to interact with p130 in physiological conditions (Hijmans et al., submitted).

Co-operation Between E2F-5 and DP-1

In DNA binding and transcriptional activity E2F-5 co-operated with DP-1. In these respects, E2F-5 possesses similar properties to other members of the E2F family. However. it is interesting to note that the co-operation between E2F-5 and DP-1 was considerably greater than, for example, the co-operation observed between E2F-1 and DP-1 in equivalent experimental conditions (for example see FIG. 14). If this assay reflects functional properties within cells, then it is possible in an intracellular environment of excess DP-1 that equivalent increases in the amount of E2F-5 and E2F-1 would result in a relatively greater level of E2F-5/DP-1 DNA binding activity. Furthermore, if there are preferred target genes for particular E2F/DP heterodimers then these differences in DNA binding activity may reflect differences in transcriptional activity.

The precise roles of the different E2F proteins in cell cycle control have yet to be established. However, it is possible that they regulate the transcriptional activity of target genes during discrete phases of cell cycle progression. For example, that E2F- 1, -2 and -3 interact with pRb (Helin et al., 1992; Kaelin et al., 1992; Ivey-Hoyle et al., 1993; Lees et al., 1993) suggests they regulate cell cycle progression through G1. In contrast, p107 associates with DRTF1/E2F towards the end of G1, peaking in S phase (Shirodkar et al., 1992) whilst p130 associates preferentially during early cell cycle progression, mostly during G0 (Cobrinik et al., 1993). However, the levels of E2F-1 and E2F-5 in a variety of cell types suggest that the expression of E2F family members is not only influenced by cell cycle phase but also by phenotype. It is possible that cells utilise a preferred subset of E2F proteins which are most suited to their cell cycle requirements.

The molecular and functional characterisation of E2F-5 reported here, together with its interaction with DP family members, indicates that a variety of heterodimers between E2F and DP family members are theoretically possible. A major goal of future studies will be to understand the physiological role of each of these transcription factors in cell cycle control

Materials and Methods

Yeast strains, media and methods. *Saccharomyces cerevisiae* strains used in this study were as follows: W3031a (Matα ade2-100 trpl-I leu2-3,112 his3-11 ura3); CTY10-5d (Matα ade2 trpl-901 leu2-3,112 his3-200 gal4 gal80 URA3::lexAop-lacZ) and PCY2 (Matα gal14 gal80 URA3::GAL1-lacZ lys2-801 his3-200 trp1-63 leu2 ade2-101) and JZ1 (Jooss et al., 1994; Matα lys2-801 ade2-10 leu2Δ1 trpΔ63 his3Δ200 URA3:: lexAop-CYC1-lacZ. Yeast strains were propagated in YPD or YNB media and transformed using a modification of the lithium acetate method. The colony colour β-galactosidase activity assay was performed by conventional procedures. β-galactosidase activity of individual transformants was quantitated in mid-log phase cultures for at least three independent transformants.

Library DNA, plasmids and oligonucleotides. pPC67 is a 14.5 d.p.c. CD-1 mouse embryo oligo dT-primed cDNA library fused downstream of yeast sequences encoding the trans activation domain of the GAL4 protein (GAD; Chevray and Nathans, 1992). Complete cDNA clones were isolated from a λZapII F9 EC library of directionally cloned poly dT-primed cDNA (Schöler et al., 1990).

Plasmid pTR27 is a derivative of pBTM116 (Bandara et al., 1993) in which the polylinker sequences have been extended; pLEX.DP-1, pGAD.E2F-1, p4xWT CYC1 and p4xMT CYC1 have been described previously (Bandara et al., 1993). pLEX(HIS).DP-1 encodes a fusion of the complete bacterial LexA protein with DP-1 (from amino acid residue 59 to 410) in the plasmid pLEX(HIS), a derivative of pBTM1 16 in which TRP1 has been replaced with HIS3. pGAD.E2F-5 contains the entire coding sequence of E2F-5 expressed as a hybrid protein with the activation domain of the yeast GAL4 protein (768–881) in the plasmid pACTII (Durfee et al., 1993). pLEX.E2F-5 contains the E2F-5 coding sequence from amino acid residue 198 to 335 expressed as a hybrid protein downstream of the complete coding sequence of the LexA protein in the plasmid pTR27. pLEX.E2F-1 carries full-length E2F-1 (1–437) in pTR27. Plasmid pG4 (previously called pG4m polyII; Webster et al., 1989) encodes the GAL4 DNA binding domain (1–148) under the control of the SV40 early promoter. Plasmid pGAL4.E2F-5 contains E2F-5 coding sequence from residue 198 to 335 fused downstream of the GAL4 sequences in pG4. Plasmids pCMVHRb, pCMVHRbΔ22, pCMV107 and pCMV107AS have been described previously (Zamanian and La Thangue, 1992; 1993). Library screening. 40 μg pPC67 library DNA was co-transformed into CTY10-5d with 40 μg pLEX(HIS).DP-1. Approximately 400,000 transformants growing on selective agar plates were screened by the in situ filter paper β-galactosidase assay. To rescue the library plasmids, blue colonies were isolated and cured of pLEX(HIS).DP-1 by growing to saturation in selective liquid media in the presence of histidine. After replica-plating on selective minimal agar, plasmid DNA from Trp$^+$ His$^-$ colonies that failed to give a blue colour when assayed for β-galactosidase was electroporated into *E.coli* HW87. Plasmids were recovered and retransformed into CTY10-5d with either pLEX(HIS).DP-1 or the control plasmid (pLEX (HIS)). A plasmid conferring a Trp$^+$ phenotype that gave a blue colony colour only in the presence of pLEX(HIS).DP-1 was selected for further analysis. To obtain a full-length cDNA, the insert was excised, radiolabelled and used to screen approximately $10^6$ plaques from the λZapII F9EC library from which a full length E2F-5 cDNA was isolated and rescued into pBluescript.

Transient transfection of 3T3 cells. Transfections and assays were performed by the conventional calcium phosphate precipitation method as described previously (Zamanian and La Thangue, 1992). β-galactosidase activity derived from pCMV-βgal as an internal control was measured as previously described (Zamanian and La Thangue, 1992).

Antisera and gel retardation analysis. Rabbit antisera raised against two distinct peptide sequences derived from E2F-5, referred to as anti-E2F-5(1), anti-E2F-5 (2) were prepared and assessed for effect on DRTF1/E2F DNA binding activity in F9 EC cell extracts as previously described (Girling et al., 1993). The E2F binding site was taken from the adenovirus E2a promoter (La Thangue et al., 1990). Either the homologous (+) or an unrelated (−) peptide was added to the DNA binding assay to assess specificity as described previously (Girling et al., 1993). The anti-DP-1 (24) antiserum was raised against a peptide derived from the C-terminal sequence of DP-1. DNA binding assays performed with GST fusion proteins were as described previously (Bandara et al., 1993; 1994). GST-DP-1, -E2F-1 (Bandara et al., 1993) and -E2F-5 (amino acid residue 2 to 335) were expressed and purified according to conventional procedures.

Northern analysis. Northern analysis of RNA levels was performed on RNA prepared from the indicated cell lines by conventional procedures. The E2F-5 probe contained 840 nucleotides extending into the 3' untranslated region. The E2F-1 probe contained the entire coding sequence of the gene generated by PCR and a probe for GAPDH served as an internal control.

REFERENCES FOR EXAMPLE 2

Bandara, L. R., Adamczewski, J. P., Hunt, T. and La Thangue, N. B. (1991). *Nature* 352, 24 9–251.

Bandara, L. R., Adamczewski, J. P., Poon, R. Y., Zamanian, M., Hunt, T. and La Thangue, N. B. (1992). *J.Cell Sci.* (Suppl.) 16, 77–85.

Bandara, L. R., Buck, V. M., Zamanian, M., Johnston, L. H. and La Thangue, N. B. (1993). *EMBO J.* 12, 4317–4324.

Bandara, L. R., Lam, E. W.-F., Sorensen, T. S., Zamanian, M., Girling, R. and La Thangue, N. B. (1994). *EMBO J.* 13, 3104–3114.

Beijersbergen, R. L., Kerkhoven, R. M., Zhu, L., Carlee, L., Voorhoeve, P. M. and Bernards, R. (1994). *Genes. Dev.* 8: 2680–2690.

Chevray, P. and D. Nathans. (1992). *Proc. Natl. Acad. Sci. USA* 89: 5789–5793.

Cobrinik, D., Whyte, P., Peeper, D. S., Jacks, T. and Weinberg, R. A. (1993). *Genes Dev.* 7, 2392–2404.

Durfee, T., Becherer, K., Chen, P.-L., Yeh, S.-H., Yang, Y., Kilburn, A. E., Lee, W.-H. and Elledge, S. J. (1993). *Genes Dev.* 7, 555–569.

Ewen, M. E., Xing, Y., Lawrence, J. B. and Livingston, D. M. (1991). *Cell* 66:1155–1164.

Fields, S. and Song, O. (1989). *Nature* 340:245–246.

Ginsberg, D., Vairo, G., Chittenden, T., Xiao, Z.-X., Xu. G., Wydner, K. L., DeCaprio, J. A., Lawrence, J. B. and Livingston, D. M. (1994). *Genes. Dev.* 8:2665–2679.

Girling, R., Partridge, J. F., Bandara, L. R., Burden, N., Totty, N. F., Hsuan, J. J. and La Thangue, N. B. (1993). *Nature* 362, 83–87.

Girling, R., Bandara, L. R., Ormondroyd, E., Lam, E. W.-F., Kotecha. S., Mohun, T. and La Thangue, N. B. (1994). *Mol. Biol. Cell.* 5, 1081–1092.

Hannon, G. J., Demetrick, D. and Beach, D. (1993). *Genes Dev.*7:2378–2391.

Heibert, S. W., Chellappan, S. P., Horowitz, J. M. and Nevins, J. R. (1992). *Genes Dev.* 6, 177–185.

Helin, K., Lees, J. A., Vidal, M., Dyson, N., Harlow, E. and Fattaey, A. (1992). *Cell* 70, 337–350.

Helin, K., Wu, C.-L., Fattaey, A. R., Lees, J. A., Dynlacht, B. D., Ngwu, C. and Harlow, E. (1993). *Genes Dev.* 7, 1850–1861.

Ivey-Hoyle, M., Conroy, R., Huber, H. E., Goodhart, P. J., Oliff, A. and Heimbrook, D. C. (1993). *Mol. Cell. Biol.* 13:7802–7812.

Jooss, K. U., Funk, M. and Muller, R. (1994). *EMBO J.* 13, 1467–1475.

Kaelin, W. G., Krek, W., Sellers, W. R., DeCaprio, J. A., Ajchenbaum, F., Fuchs, C. S., Chittenden, T., Li, Y., Farnham, P. J., Blanar, M. A., Livingston, D. M. and Flemington, E. K. (1992). *Cell* 70, 351–364.

Krek, W., Livingston, D. M. and Shirodkar, S. (1993). *Science* 262, 1557–1560.

Krek, W., Ewen, M. E., Shirodkar, S., Arany, Z., Kaelin, W. G. and Livingston, D. M. (1994). *Cell* 78, 161–172.

La Thangue, N. B. (1994). *Trends Biochem. Sci.* 19, 108–114.

La Thangue, N., Thimmappaya, B. and Rigby, P. W. J. (1990). *Nucl. Acids. Res.* 18, 2929–2938.

Lam, E. W.-F. and La Thangue, N. B. (1994). *Curr. Op. Cell Biol.* 6, 859–866.

Lees, E., Fahar, B., Dulic, V., Reed, S. I. and Harlow, E. (1992). *Genes Dev.* 6, 1874–1885.

Lees, J. A., Saito, M., Vidal, M., Valentine, M., Look, T., Harlow, E., Dyson, N. and Helin, K. (1993). *Mol. Cell. Biol.* 13:7813–7825.

Li, Y., Graham, C., Lacy, S., Duncan, A. M. V. and Whyte, P. (1993). *Genes Dev.* 7:2366–2377.

Nevins, J. R. (1992). *Science* 258, 424–429.

Schwarz, J. K., Devoto, S. H., Smith, E. J., Chellappan, S. P., Jakoi, L. and Nevins, J. R. (1993). *EMBO J.* 12, 1013–1020.

Schöler, H. R., Ruppert, S., Suzuki, N., Chowdhury, K. and Gruss, P. (1990). *Nature* 344, 435–439.

Shan, B., Zhu, X., Chen, P. L., Durfee, T., Yang, Y., Sharp, D. and Lee, W. H. (1992). *Mol. Cell. Biol.* 12 5620–5631.

Shirodkar, S., Ewen, M., DeCaprio, J. A., Morgan, J., Livingston, D. M. and Chittenden, T. (1992). *Cell* 68, 157–166.

Webster, N. J. G., Green, S., Tasset, D., Ponglikitmongkol, M. and Chambon, P. (1989). *EMBO J.,* 8, 1441–1446.

Zamanian, M. and La Thangue, N. B. (1992). *EMBO J.* 11:2603–2610.

Zamanian, M. and La Thangue, N. B. (1993). *Mol. Biol. Cell.* 4:389–396.

---

What is claimed is:

1. An isolated E2F-5 polypeptide selected from the group of:

the polypeptide comprising SEQ ID NO:2;

the polypeptide comprising SEQ ID NO:4;

a polypeptide comprising a fragment of SEQ ID NO:2 of at least 60 amino acids, said fragment being capable of forming a transactivation complex with a DP protein; and a polypeptide comprising a fragment of SEQ ID NO:4 of at least 60 amino acids, said fragment being capable of forming a transactivation complex with a DP protein.

2. An isolated polypeptide comprising SEQ ID NO:2.

3. An isolated polypeptide comprising SEQ ID NO:4.

4. An Isolated polypeptide comprising a fragment of at least 60 amino acids of the isolated polypeptide of claim 2 or 3 said fragment being capable of forming a transactivation complex with a DP protein.

5. The isolated polypeptide of claim 1 that is detectably labeled.

6. The isolated polypeptide of claim 1 fixed to a solid phase.

7. A composition comprising the polypeptide according to claim 1 together with a carrier or diluent.

8. A screening assay for identifying an inhibitor of E2F-5/DP complex formation, which assay comprises:

bringing into contact:
   (i) a DP polypeptide, said DP polypeptide being a component of an E2F transcription factor;
   (ii) the E2F-5 polypeptide of claim 1; and
   (iii) a putative inhibitor;

under conditions in which the components (i) and (ii) in the absence of said putative inhibitor are able to form a complex; and determining the extent to which, if any, the presence of said putative inhibitor is able to disrupt the formation of the complex.

9. The screening assay of claim 8 wherein said determining is made by examining the ability of said complex to bind or activate an E2F DNA binding site in vitro.

10. The screening assay of claim 8 wherein the putative inhibitor is a fragment of 10 or more amino acids of the polypeptide of claim 2.

11. An assay according to claim 8 which further comprises selecting as an inhibitor of E2F-5/DP complex formation a compound capable of so disrupting said complex formation.

* * * * *